(12) United States Patent
Gurumohan et al.

(10) Patent No.: US 11,099,166 B2
(45) Date of Patent: Aug. 24, 2021

(54) CONTAINER CONTENT QUANTITY MEASUREMENT AND ANALYSIS

(71) Applicant: Nectar, Inc., Palo Alto, CA (US)

(72) Inventors: Prabhanjan C. Gurumohan, Mountain View, CA (US); Aayush Phumbhra, Palo Alto, CA (US)

(73) Assignee: NECTAR, INC., Mountain View, CA (US)

( * ) Notice: Subject to any disclaimer, the term of this patent is extended or adjusted under 35 U.S.C. 154(b) by 0 days.

(21) Appl. No.: 14/676,432

(22) Filed: Apr. 1, 2015

(65) Prior Publication Data

US 2015/0285775 A1    Oct. 8, 2015

Related U.S. Application Data

(63) Continuation-in-part of application No. 14/627,719, filed on Feb. 20, 2015, now Pat. No. 10,072,964.

(60) Provisional application No. 62/093,890, filed on Dec. 18, 2014, provisional application No. 62/006,419, filed on Jun. 2, 2014, provisional application No. 61/975,337, filed on Apr. 4, 2014.

(51) Int. Cl.
*G01F 23/296* (2006.01)
*G01N 33/02* (2006.01)
*G01D 11/24* (2006.01)
*G06Q 10/08* (2012.01)

(52) U.S. Cl.
CPC ............ *G01N 33/02* (2013.01); *G01D 11/24* (2013.01); *G06Q 10/087* (2013.01); *G01F 23/2962* (2013.01)

(58) Field of Classification Search
CPC ............................ G01N 33/02; G01F 23/2962
See application file for complete search history.

(56) References Cited

U.S. PATENT DOCUMENTS

| 2,804,103 | A |   | 8/1957  | Wall      |              |
|-----------|---|---|---------|-----------|--------------|
| 4,386,409 | A | * | 5/1983  | Petroff   | G01F 23/2962 |
|           |   |   |         |           | 367/108      |
| 4,697,200 | A |   | 9/1987  | Miyatake  |              |
| 4,698,541 | A |   | 10/1987 | Bar-Cohen |              |

(Continued)

FOREIGN PATENT DOCUMENTS

| CN | 101726343 A | 6/2010 |
|----|-------------|--------|
| CN | 103815675 A | 5/2014 |
| WO | 2016037612  | 3/2016 |

OTHER PUBLICATIONS

Amanda MacMillan. It's the Water Bottle of the Future-and You can Pre-Order It Now! Fitness (Flash/Fitness-Blog/) Oct. 7, 2013. http://www.self.com/flash/fitness-blog/2013/10/fitness-water-bottle-of-the-future/.

(Continued)

*Primary Examiner* — Lisa M Caputo
*Assistant Examiner* — Alex T Devito

(57) ABSTRACT

Quantity analysis is disclosed. A quantity identification of an amount of content included in a container is received from a container cover of the container. The quantity identification is analyzed along with a history of past quantity identifications received from the container cover over time to determine an analysis result. An action associated with the content of the container is performed based on the analysis result.

27 Claims, 18 Drawing Sheets

(56) References Cited

U.S. PATENT DOCUMENTS

| | | | |
|---|---|---|---|
| 4,723,305 A * | 2/1988 | Phillips | H01Q 5/35 343/702 |
| 4,782,451 A * | 11/1988 | Mazzarella | G01F 23/0069 340/680 |
| 4,823,600 A | 4/1989 | Biegel | |
| 4,934,191 A | 6/1990 | Kroening | |
| 4,961,456 A | 10/1990 | Stembridge | |
| 5,042,698 A | 8/1991 | Fessell | |
| 5,085,077 A * | 2/1992 | Stapleton | G01F 23/2962 340/621 |
| 5,150,334 A | 9/1992 | Crosby | |
| 5,303,585 A | 4/1994 | Lichte | |
| 5,389,848 A | 2/1995 | Trzaskos | |
| 5,471,872 A | 12/1995 | Cummings | |
| 5,603,430 A | 2/1997 | Loehrke | |
| 5,793,705 A | 8/1998 | Gazis | |
| 5,866,815 A | 2/1999 | Schwald | |
| 5,880,364 A | 3/1999 | Dam | |
| 6,272,921 B1 * | 8/2001 | Ivanovich | G01F 23/2966 73/290 V |
| 6,545,946 B1 | 4/2003 | Huss | |
| 6,856,247 B1 | 2/2005 | Wallace | |
| 7,068,805 B2 | 6/2006 | Geddes | |
| 7,088,258 B2 | 8/2006 | Morrison | |
| 7,109,863 B2 | 9/2006 | Morrison | |
| 7,190,278 B2 | 3/2007 | Morrison | |
| 7,495,558 B2 | 2/2009 | Pope et al. | |
| 7,573,395 B2 | 8/2009 | Morrison | |
| 7,598,883 B2 | 10/2009 | Morrison | |
| 8,061,198 B2 | 11/2011 | Yinko et al. | |
| 8,151,596 B2 | 4/2012 | Richmond et al. | |
| 8,284,068 B2 | 10/2012 | Johnson | |
| 8,453,878 B2 | 6/2013 | Palmquist | |
| 8,851,740 B1 | 10/2014 | Mills | |
| 8,981,793 B2 | 3/2015 | Mukherjee | |
| 9,506,798 B2 | 11/2016 | Saltzgiver | |
| 9,508,484 B2 | 11/2016 | Scholz | |
| 9,576,267 B2 | 2/2017 | Kundra | |
| 9,911,290 B1 | 3/2018 | Zalewski | |
| 10,078,003 B2 | 9/2018 | Gurumohan | |
| 10,127,520 B2 | 11/2018 | Kundra | |
| 10,161,782 B2 | 12/2018 | Saltzgiver | |
| 10,219,641 B2 | 3/2019 | Liao | |
| 10,267,667 B2 | 4/2019 | Gurumohan | |
| 10,324,075 B2 | 6/2019 | Gurumohan | |
| 10,670,444 B2 | 6/2020 | Gurumohan | |
| 2002/0059828 A1 | 5/2002 | Muller | |
| 2002/0070861 A1 | 6/2002 | Teller | |
| 2003/0037613 A1 | 2/2003 | Mulrooney | |
| 2004/0169600 A1 | 9/2004 | Haynes | |
| 2005/0033532 A1 | 2/2005 | Mogadam | |
| 2005/0072226 A1 | 4/2005 | Pappas | |
| 2005/0087255 A1 | 4/2005 | Humphrey | |
| 2005/0090743 A1 | 4/2005 | Kawashima | |
| 2005/0268715 A1 | 12/2005 | Sabatino | |
| 2006/0154642 A1 | 7/2006 | Scannell | |
| 2006/0201245 A1 | 9/2006 | Huber | |
| 2006/0231109 A1 | 10/2006 | Howell et al. | |
| 2006/0270421 A1 * | 11/2006 | Phillips | G08B 21/0236 455/457 |
| 2007/0008212 A1 * | 1/2007 | Serban | H01Q 13/02 342/124 |
| 2007/0125162 A1 | 6/2007 | Ghazi et al. | |
| 2007/0191983 A1 | 8/2007 | Griffits | |
| 2007/0261487 A1 | 11/2007 | Sintes | |
| 2008/0036615 A1 | 2/2008 | Lyall, III | |
| 2008/0147211 A1 | 6/2008 | Teller | |
| 2008/0154522 A1 | 6/2008 | Welle | |
| 2008/0250869 A1 | 10/2008 | Breed | |
| 2008/0297403 A1 | 12/2008 | Aakerstroem | |
| 2008/0314807 A1 | 12/2008 | Junghanns | |
| 2009/0093983 A1 | 4/2009 | Trafford | |
| 2009/0105969 A1 | 4/2009 | Saylor | |
| 2009/0134183 A1 | 5/2009 | Odishoo | |
| 2009/0289835 A1 | 11/2009 | Edvardsson | |
| 2010/0070270 A1 | 3/2010 | Sai | |
| 2010/0101317 A1 | 4/2010 | Ashrafzadeh | |
| 2010/0108635 A1 | 5/2010 | Horstman | |
| 2010/0200593 A1 | 8/2010 | Lazar et al. | |
| 2010/0270257 A1 | 10/2010 | Wachman et al. | |
| 2011/0042408 A1 * | 2/2011 | Giordano | A47J 31/44 222/23 |
| 2011/0166699 A1 | 7/2011 | Palmquist | |
| 2011/0169635 A1 | 7/2011 | Johnson | |
| 2012/0052802 A1 | 3/2012 | Kasslin | |
| 2012/0206155 A1 | 8/2012 | Wang et al. | |
| 2013/0002443 A1 | 1/2013 | Breed | |
| 2013/0073218 A1 | 3/2013 | Haas | |
| 2013/0122817 A1 | 5/2013 | Pivaudran | |
| 2013/0222135 A1 | 8/2013 | Stein et al. | |
| 2013/0313204 A1 * | 11/2013 | Shalon | G01N 33/18 210/744 |
| 2014/0149265 A1 | 5/2014 | Kundra | |
| 2014/0208845 A1 | 7/2014 | Zlotnick | |
| 2014/0251850 A1 | 9/2014 | Huang | |
| 2014/0324585 A1 | 10/2014 | Mederos | |
| 2014/0360270 A1 | 12/2014 | Koenig et al. | |
| 2015/0101405 A1 | 4/2015 | Gorenflo | |
| 2015/0285775 A1 | 10/2015 | Gurumohan | |
| 2015/0334079 A1 | 11/2015 | Laidlaw | |
| 2015/0355012 A1 | 12/2015 | Gurumohan | |
| 2016/0025545 A1 | 1/2016 | Saltzgiver | |
| 2016/0137483 A1 | 5/2016 | Pfeiffer | |
| 2016/0146659 A1 | 5/2016 | Saltzgiver | |
| 2016/0178426 A1 | 6/2016 | Gurumohan | |
| 2016/0194190 A1 | 7/2016 | Fogg | |
| 2016/0198246 A1 | 7/2016 | Gurumohan | |
| 2016/0264394 A1 | 9/2016 | Hershberger | |
| 2017/0027229 A1 | 2/2017 | Cameron | |
| 2017/0161676 A1 | 6/2017 | Aji | |
| 2017/0292870 A1 | 10/2017 | Carter | |
| 2017/0332813 A1 | 11/2017 | Liao | |
| 2017/0337496 A1 | 11/2017 | Jones | |
| 2017/0337535 A1 | 11/2017 | Jones | |
| 2017/0340147 A1 | 11/2017 | Hambrock | |
| 2017/0341830 A1 | 11/2017 | Nishizawa | |
| 2018/0164143 A1 | 6/2018 | Gurumohan | |
| 2018/0202853 A1 | 7/2018 | Boström | |
| 2018/0328776 A1 | 11/2018 | Gurumohan | |
| 2019/0274456 A1 | 9/2019 | Hambrock | |
| 2020/0033179 A1 | 1/2020 | Gurumohan | |
| 2020/0056919 A1 | 2/2020 | Jones | |
| 2020/0172387 A1 | 6/2020 | Hershberger | |

OTHER PUBLICATIONS

Jonah Comstock. Slideshow: 8 Pillboxes that Connect to Your Phone. Mobihealth News. Mar. 13, 2013. http://mobihealthnews.com/20795/slideshow-8-pillboxes-that-connect-to-your-phone/2/.

Kreutzer et al., "Radio Frequency Identification Based Detection of Filling Levels for Automated Monitoring of Fluid Intake", Dec. 5, 2014, Proceedings of the 2014 IEEE International Conference on Robotics and Biomimetics, pp. 2049-2054.

Matthew Tait, "Smart Drink Bottle", Sep. 10, 2018, ip.com, IPCOM000255205D, pp. 1-23.

Sing et al., "A Microcontroller-based System for Liquid Level Detection Using Infrared Sensing", 2015, 2015 IEEE Student Conference on Research and Development (SCOReD), pp. 294-299.

* cited by examiner

CONTAINER CONTENT QUANTITY MEASUREMENT AND ANALYSIS

CROSS REFERENCE TO OTHER APPLICATIONS

This application claims priority to U.S. Provisional Patent Application No. 61/975,337 entitled SYSTEMS AND METHODS FOR CONSUMER FOOD AND NUTRITION MANAGEMENT filed Apr. 4, 2014 which is incorporated herein by reference for all purposes.

This application claims priority to U.S. Provisional Patent Application No. 62/006,419 entitled SYSTEM AND METHODS FOR FOOD AND BEVERAGE TRACKING, REPLENISHMENT AND CONSUMPTION MANAGEMENT filed Jun. 2, 2014 which is incorporated herein by reference for all purposes.

This application is a continuation in part of co-pending U.S. patent application Ser. No. 14/627,719 entitled CONTAINER FILL LEVEL MEASUREMENT AND MANAGEMENT filed Feb. 20, 2015, which is incorporated herein by reference for all purposes; which claims priority to U.S. Provisional Patent Application No. 62/093,890 entitled CONTAINER FILL LEVEL MEASUREMENT AND MANAGEMENT filed Dec. 18, 2014 which is incorporated herein by reference for all purposes.

BACKGROUND OF THE INVENTION

Often food distribution requires individuals, families and households to make repeated visits to a brick and mortar grocery store to shop for dairy, fresh produce and staples. Although delivery services exists, utilization of these services often require a manual intervention from the user to check the remaining quantity of food and beverages and make a conscious effort to reorder desired items. Often consumers either waste food due to excess or a failure to buy what's needed at the right time.

BRIEF DESCRIPTION OF THE DRAWINGS

Various embodiments of the invention are disclosed in the following detailed description and the accompanying drawings.

DETAILED DESCRIPTION

Figure 1:
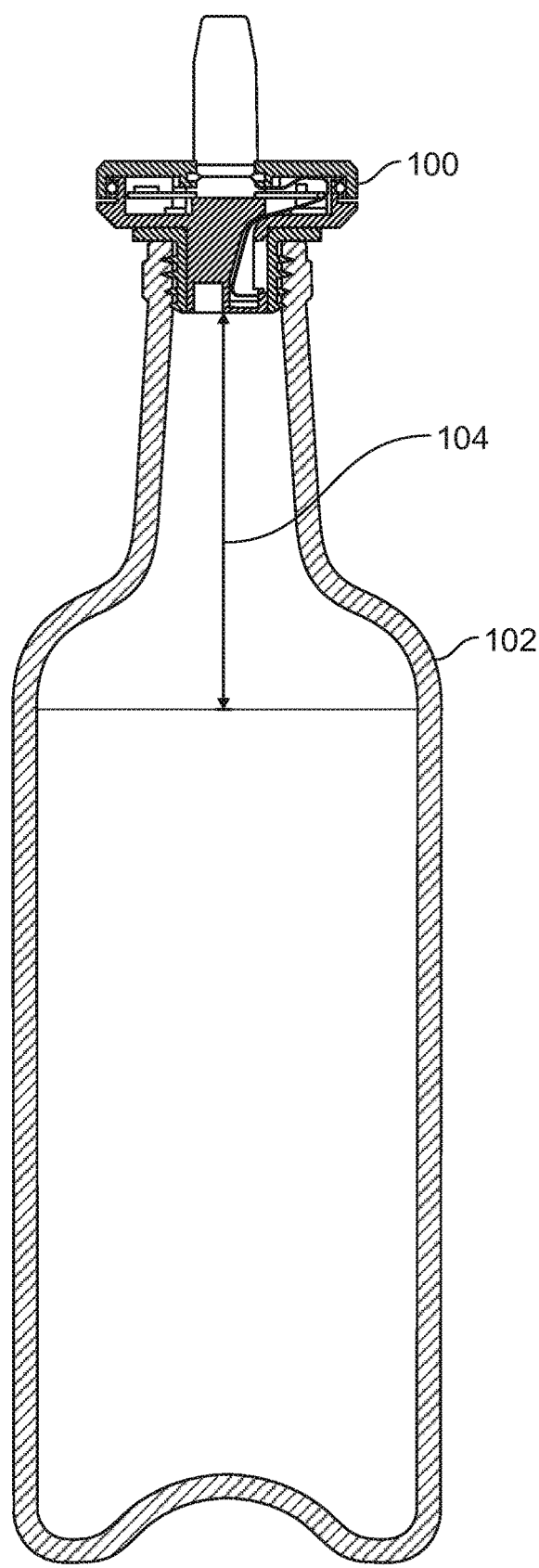
FIG. 1 is a diagram illustrating an embodiment of a fill level sensor engaged in a container.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

In some embodiments, one or more devices help users track remaining quantity and expiration of food (e.g., including beverages). These include a new container cover (e.g., bottle cap) for containers (e.g., bags, food containers, boxes, bags, etc.), clips, stickers (e.g., touch sensitive), markers, patches, and a receipt scanner. The container cover and scanner may help consumers track the food quantities included in the container and transmit them to a cloud based analysis system. The analysis system in turn may identify and associate the food quantity and expiration with food and beverages owned by a unique consumer who has been associated with registered devices. In some embodiments, the analysis system learns the consumption pattern and nutrients of the food items being tracked and also learns the consumer interests in various types of foods, food preferences and their health preferences.

The analysis system may transmit notifications to consumer mobile devices via a mobile application installed/accessed on the mobile devices. The mobile application may inform the user about quantity of food (e.g., quantity remaining), food expiration, health improvements, recipes, and/or seasonal recommendations. It may also offer a marketplace to order food from various sources, including delivery services that offer the most convenient way to receive the food. It may also provide recommendations on ordering food/beverages that may be needed to prepare a certain recipe that's based on seasonality, interests, and social recommendations. The mobile application may also help remind and notify a user to pick up certain food item when it is running low or about to expire. For example, notification is provided when the user is physically near a merchant where the food item can be obtained.

In some embodiments, a fill level sensor of a container cover, clip, sticker, marker and/or patch measures the amount of liquid contained in a container. In some embodiments, the fill level sensor includes an acoustic transmitter located proximal to a portion of a container cover that is configured to engage a container opening. For example, the fill level sensor is included in a cap of a bottle and includes a speaker that will transmit a signal that will be utilized to measure a liquid fill level of the bottle. In some embodiments, the fill level sensor also includes a waveguide extending from the transmitter such that the waveguide includes a distal end that is configured to be located within the container interior when the container cover engages the container. For example, the waveguide guides a signal transmitted by the transmitter to a desired location and direction where the signal is directed towards contents filling a container. The signal may reflect off the container contents and arrive at a receiver of the fill level sensor that analyzes the received reflected signal to determine the fill level of the container.

FIG. 1 is a diagram illustrating an embodiment of a fill level sensor engaged in a container. Container 102 is filled with a liquid. In the example shown, fill level sensor 100 is configured as a bottle cap with a spout. The liquid fill level of container 102 may be determined by measuring the distance between sensor 100 and the liquid surface of container 102. As shown by line 104, a transmitter of sensor 100 sends out a signal (e.g., ultrasonic signal) that gets reflected by the surface of the liquid. The reflected signal is detected by a receiver of sensor 100.

By measuring the amount of time it took to receive the reflected signal, the distance traveled by the signal before being reflected (e.g., distance between sensor 100 and liquid surface is half of the total distance traveled by the signal) may be determined by multiplying the amount of time by the speed of the signal (e.g., speed of sound).

In some embodiments, to determine the amount of time it took to receive the reflected signal, the received reflected signal is filtered to isolate the desired signal (e.g., band-pass filter the received signal), amplified, and analyzed to detect peaks that correspond to when the reflected signal was received. A predetermined beginning portion (e.g., predetermined amount of time in the beginning of the signal) of the received signal may be ignored when analyzing the signal to ignore signals that were detected due to coupling between the transmitter and receiver of sensor 100. For example, when the transmitter transmits the signal, the signal may be received by the receiver of sensor 100 (e.g., conducted through sensor 100, due to undesired reflection, etc.) before the signal is reflected by the contents of the container, and the undesired received signals received in the beginning portion of the received signal are ignored when identifying the desired received reflected signal.

If the total distance between the bottom of container 102 and sensor 100 is known, the fill height of container 102 can be determined (e.g., total distance between bottom and sensor 100 minus distance between sensor 100 and liquid surface). If the shape and volume of the bottle are known, the volume of liquid contained in container 102 may be determined. For example, a table/database/data structure that maps fill level (e.g., fill height, height between liquid surface and sensor 100, etc.) to liquid volume of the container is utilized to determine liquid volume corresponding to the determined fill level. Different tables/databases/data structures may exist for different types of containers.

Sensor 100 includes a transmitter for transmitting the reflected signal and a receiver for receiving the reflected signal. However, due to the narrow opening of container 102, the placement of the transmitter and receiver in sensor 100 is limited to the narrow configuration of the bottle opening. If the transmitter and receiver are placed too close together, the transmitter and receiver may become coupled together. For example, the receiver may receive a strong signal from the transmitter as soon as the transmitter transmits a signal and the receiver may require a long settling time before the receiver is able to detect the desired reflected signal. If the distance between sensor 100 and the liquid surface is small, the desired reflected signal may be received before the receiver has settled and the receiver is unable to detect the desired reflected signal. In some embodiments, the transmitter and receiver of sensor 100 are vertically offset from each other to create a desired amount of separation distance between the transmitter and receiver. The separation distance may reduce the coupling of the transmitter and receiver and allow dampening of the transmitted signal propagated between the transmitter and the receiver through sensor 100. However, the vertical separation of the transmitter and the receiver may create undesired reflections within the container (e.g., reflections from the neck of a bottle) that make it difficult to identify the signal reflected from the liquid surface. In some embodiments, a waveguide extending from the transmitter is utilized to direct the signal transmitted by the transmitter towards the desired direction and location to minimize undesired effects.

Figure 2A:
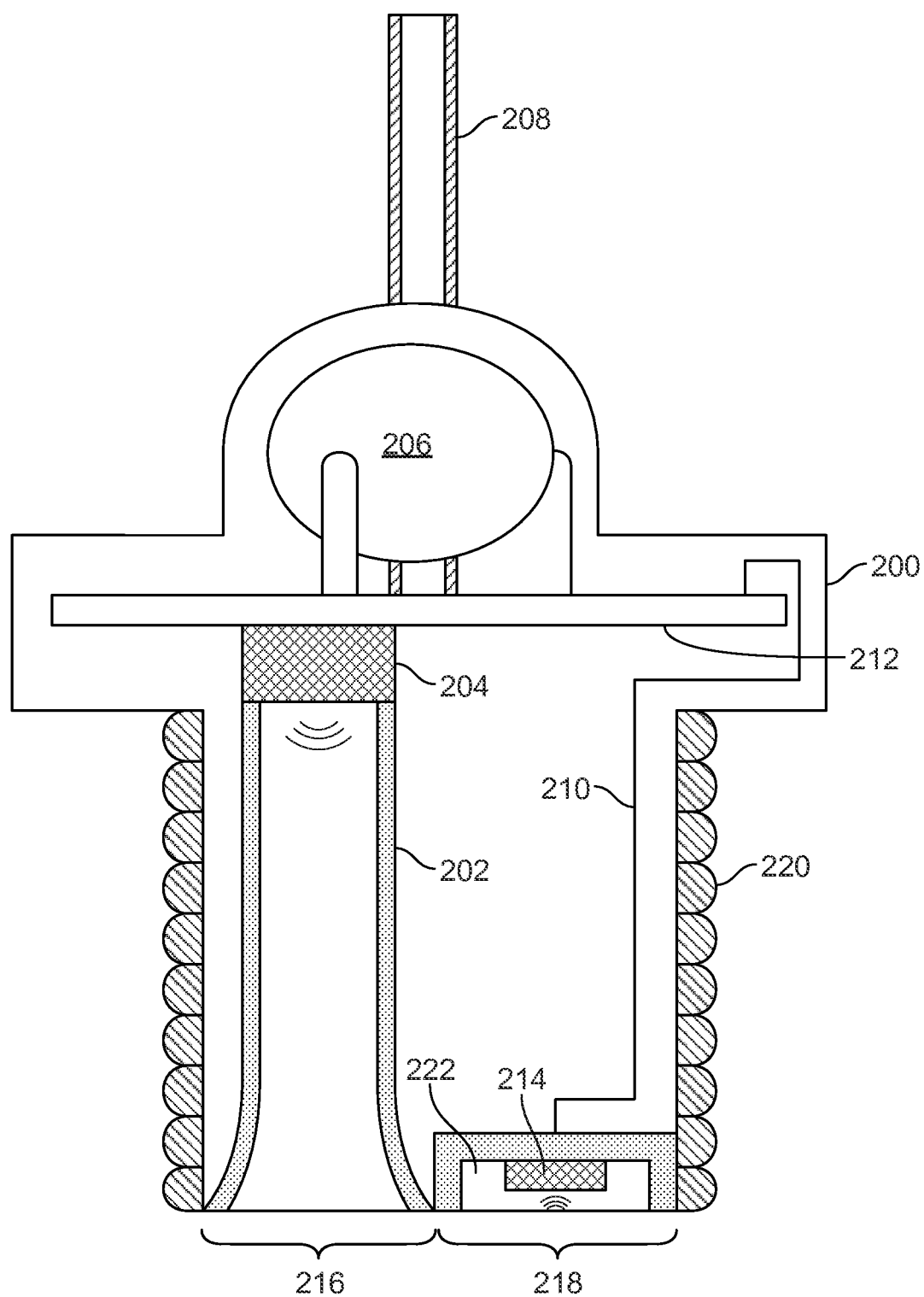
FIG. 2A is a vertical cross-sectional diagram illustrating an embodiment of a fill level sensor.
Figure 2B:
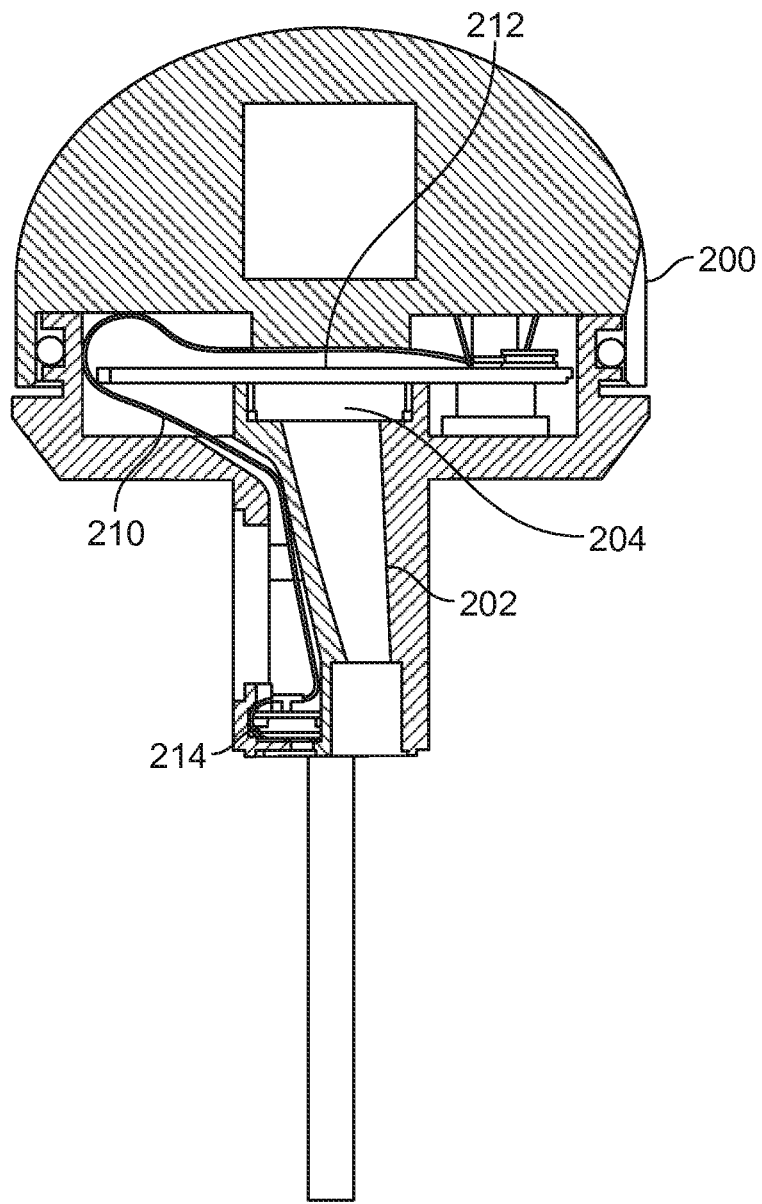
FIG. 2B is a vertical cross-sectional diagram illustrating an alternative embodiment of a fill level sensor.

FIG. 2A is a vertical cross-sectional diagram illustrating an embodiment of a fill level sensor. In some embodiments, sensor 200 is sensor 100 of FIG. 1. FIG. 2B is a vertical cross-sectional diagram illustrating an alternative embodiment of a fill level sensor. In the examples shown, sensor 200 is configured as a bottle stopper with a spout. As shown in FIG. 2A, sensor 200 includes flexible container coupling ridges 220 (e.g., rubber rings) that allows sensor 200 to be coupled to and seal an opening of a container (e.g., as shown in FIG. 1). However, in other embodiments, sensor 200 may be configured as a different cover of a container. For example, the components of sensor 200 may be included in a screw-on cap or any other cap that engages a container.

Sensor 200 includes circuit board 212. For example circuit board 212 is a printed circuit board. Circuit board 212 may connect together one or more of the following: a processor, a memory, a data storage, a connector, an integrated chip, a transmitter, a receiver, an accelerometer, a tilt sensor, a solar panel, a display, a gyroscope, a wireless data communication signal transmitter (e.g., a component able to communicate using Bluetooth, Wi-Fi, other wireless protocol, etc.), and other electrical components. For example, a processor connected to circuit board 212 provides a command to transmit an acoustic signal using a transmitter and processes a received signal to determine a fill level indicator. The fill level indicator may be transmitted wirelessly to another device such as a mobile device, a computer, a display device, or any other computing or display device using a wireless data communication transmitter. Circuit board 212 is connected to battery 206. Battery 206 provides power to the circuit of circuit board 212. Battery 206 may be rechargeable and/or replaceable. The housing of sensor 200 may be composed of one or more materials. Examples of the materials include a food grade polymer, plastic, rubber, stainless steel, and other metals.

Sensor 200 includes spout 208. Spout 208 is a part of a channel (e.g., tube) that allows container contents (e.g., liquid) to pass through to the tip opening of spout 208 from a bottom of sensor 200. For example, a liquid contained in a container that is capped by sensor 200 is able to pass through sensor 200 and exit the opening of spout 208 when the container capped by sensor 200 is tipped over. In some embodiments, circuit board 212 includes a hole that accommodates the channel (e.g., tube) that allows container contents (e.g., liquid) to pass through the circuit board. In other embodiments, spout 208 may not exist in sensor 200. In some embodiments, sensor 200 includes a vent pipe (not shown) that allows air to enter a container capped by sensor 200 as a content of the container is poured out through spout 208. In some embodiments, sensor 200 includes a motor (not shown) that pumps out contents of the container capped by sensor 200.

Circuit board 212 is connected to transmitter 204. In some embodiments, transmitter 204 is an acoustic transmitter (e.g., ultrasonic signal transmitter). For example, transmitter 204 is a speaker. In some embodiments, transmitter 204 is a piezoelectric speaker. In some embodiments, transmitter 204 is configured to transmit a signal within the ultrasonic frequencies. In some embodiments, transmitter 204 is configured to transmit a signal between 20 kHz and 400 kHz, inclusive. In some embodiments, transmitter 204 is configured to transmit a 29 kHz signal. In some embodiments, transmitter 204 is an acoustic impulse generator.

Receiver 214 is connected to circuit board 212 via connector 210. Examples of connector 210 include a wire, a bus, a flexible printed circuit board, and any other connector able to transmit a signal. In some embodiments, receiver 214 is an acoustic receiver (e.g., ultrasonic signal receiver). In some embodiments, receiver 214 is a microphone. In some embodiments, receiver 214 is a microelectromechanical systems (MEMS) microphone. For example, receiver 214 is 2 millimeter×3 millimeter in size.

Waveguide 202 extends from transmitter 204. For example, waveguide 202 includes a hollow chamber (e.g., tube) that guides and propagates an acoustic signal emitted by transmitter 204 from one end of the chamber to the other end of the chamber. For example, signal emitted by transmitter 204 enters waveguide 202 at the signal input end of the hollow chamber and exits out its output end of the hollow chamber (e.g., distal end). In some embodiments, waveguide 202 aids in directing an acoustic signal (e.g., ultrasonic signal, acoustic impulse) emitted by transmitter 204 towards the direction of the distance to be measured (e.g., towards bottom of sensor 200 that will be facing contents of a container capped by sensor 200).

In some embodiments, it is desirable to reduce and/or attempt to eliminate any signal reflections within the chamber of waveguide 202 as the signal is guided from one end to the other end of waveguide 202. For example, any undesired reflection may mask and hinder detection of the signal reflected by container contents desired to be detected. Any sudden change in the shape of the hollow chamber may create an impedance mismatch that creates a reflection within the hollow chamber of waveguide 202. In some embodiments, the interior wall of the hollow chamber of waveguide 202 is substantially smooth to prevent impedance mismatches. In some embodiments, a shape and/or size of a horizontal cross section of waveguide 202 does not change by more than one percent per millimeter of vertical distance between the signal input end closest to transmitter 204 to the other signal output end (e.g., distal end). In some embodiments, a shape of the opening of one end of the hollow chamber is different from a shape of the opening of the other end of the hollow chamber. For example, a shape of an opening of the transmitter may be different than a desired shape of the signal output end of waveguide 202 (e.g., desired shape to improve directionality of the signal in container). In one example, the signal input end of the chamber of waveguide 202 is shaped in a first shape (e.g., elliptical shape) and the output opening end of the other end of the chamber of waveguide 202 is shaped in a second shape (e.g., circular shape). The change in horizontal cross-sectional shape of the hollow signal propagation chamber may gradually morph from the first shape to the second shape across the vertical length of waveguide 202. For example, the minor axis of the elliptical shape signal input opening gradually is expanded (e.g., flair out smoothly) to generally match the major axis of the elliptical shape in the output end of waveguide 202.

In some embodiments, a cross-sectional area of a signal output opening of the chamber of waveguide 202 is at least as large as a cross-sectional area of a signal input opening of the other end of the chamber of waveguide 202 that receives the signal from transmitter 204. For example, the cross-sectional area of the signal output opening of waveguide 202 is substantially equal to the cross-sectional area of the signal input opening in one embodiment. In another example, the cross-sectional area of the signal output opening of waveguide 202 is greater than the cross-sectional area of the signal input opening.

In some embodiments, the horizontal cross-sectional area of the hollow chamber of waveguide 202 is only greater or equal to a previous horizontal cross-sectional area of the hollow chamber from the input opening to the output opening of waveguide 202. For example, in order to ensure that the amplitude of an acoustic signal outputted by transmitter 204 is maintained as much as possible, the cross-sectional area of the chamber of waveguide 202 never decreases as the acoustic signal is traveling down the chamber of waveguide 202. In some embodiments, the horizontal cross-sectional area of the chamber of waveguide 202 is generally increasing as the signal emitted by transmitter 204 travels down waveguide 202 towards the distal end of waveguide 202.

In some embodiments, the interior hollow chamber of waveguide 202 is coated with a dampening material. For example, an acoustic signal dampening material (e.g., rubber like material) coats plastic walls of the hollow chamber and the coating may assist in reducing the amount of signal that gets transferred to receiver 214 from the portion of the signal that impacts the walls of the hollow chamber. In some embodiments, an interior chamber of waveguide 200 is filled with an acoustically permeable material. In some embodiments, an open end of waveguide 202 is touching transmitter 204. For example, a rubberized end of waveguide 202 seals signals emitted by transmitter 204 within an air chamber of waveguide 202. In some embodiments, a size of a signal input opening of waveguide 202 near transmitter 204 is at least as large as a transmitter opening of transmitter 204. For example, transmitter 204 includes an opening where an acoustic signal is outputted (e.g., speaker grill opening) and the opening of the transmitter is positioned within the signal input opening of waveguide 202 that is at least as large. In some embodiments, a shape and size of a signal input opening of waveguide 202 near transmitter 204 is substantially the same as a transmitter opening of transmitter 204. In some embodiments, waveguide 202 is attached to transmitter 204. For example, transmitter 204 and waveguide 202 are attached together by glue. In some embodiments, waveguide 202 is mechanically coupled to transmitter 204.

In some embodiments, a height of waveguide 202 (e.g., distance between the input and output openings) is approximately 20 millimeters. In some embodiments, a height of waveguide 202 (e.g., distance between the input and output openings) is approximately less than or equal to 60 millimeters. In some embodiments, widths of a hollow chamber of waveguide 202 (e.g., horizontal cross-sectional area) is approximately is less than or equal to 12 millimeters. In various embodiments, the shape, length, and width of waveguide 202 may be any combination of shape, length and width configurations and sizes.

In some embodiments, waveguide 202 is attached to receiver chamber 222 of receiver 214. For example as shown, receiver 214 is recessed in receiver chamber 222 area that is included/attached to the side of waveguide 202. Waveguide 202 and receiver chamber 222 may be composed of the same or different materials. Examples of the materials include a food grade polymer, plastic, rubber, stainless steel, and other metals. In some embodiments, waveguide 202 is not attached to receiver chamber 222. For example, receiver chamber 222 is attached to the housing of sensor 200 and not directly attached to waveguide 202.

In some embodiments, a placement distance (e.g., vertical distance) between transmitter 204 and receiver 214 is at least 0.6 millimeters. For example, by vertically offsetting the transmitter 204 and receiver 214, signal coupling between transmitter 204 and receiver 214 through materials of sensor 200 is reduced and allows better detection of a desired reflected signal received by receiver 214. In some embodiments, at least a portion of transmitter 204 horizontally overlaps receiver 214 in the horizontal position. For example, due to their vertical offset, transmitter 204 is able to horizontally overlap receiver 214 (e.g., at least a portion of width of transmitter 204 overlaps at least a portion of width of receiver 214). In some embodiments, the signal output opening of waveguide 202 is substantially on the same vertical location as the opening of receiver chamber 222. For example, by placing the signal output opening of waveguide 202 on the same vertical location as the opening of receiver chamber 222, an effect of a signal reflection caused by the impedance mismatch of the output opening of waveguide 202 on the detection of a desired received reflected signal is minimized. In some embodiments, the signal output opening of waveguide 202 is parallel to the opening of receiver chamber 222.

In some embodiments, because debris, liquid, and other materials may enter the chamber of waveguide 202 and receiver chamber 222 (e.g., when using spout 208 to pour out contents of the container), the chamber of waveguide 202 and receiver chamber 222 are protected (e.g., to protect transmitter 204 and receiver 214). In some embodiments, a protective layer material covers the output opening of waveguide 202 and the opening of receiver chamber 222. Ideally the protective material must not allow undesired material through to the chambers while at the same time allowing signals (e.g., acoustic signals) to pass through. Protective material 216 covers the output opening of waveguide 202 and is attached to the opening edges of waveguide 202. Protective material 218 covers the output opening of receiver chamber 222 and is attached to the opening edges of receiver chamber 222. In some embodiments, protective material 216 and protective material 218 are the same continuous material. For example, a single connected sheet includes both protective material 216 and protective material 218. In some embodiments, protective material 216 and protective material 218 are not continuous materials. For example, in order to maximize decoupling of the transmitted signal of transmitter 204 and the received signal of receiver 214, protective material 216 and protective material 218 are not made of the same continuous material. In some embodiments, protective material 216 and protective material 218 are different materials. Examples of protective material 216 and protective material 218 include one or more of the following: mylar sheet, waterproof mesh, acoustic sheet, Teflon, Gortek and any other appropriate mesh or membrane. For example, a mylar sheet covering does not allow liquid to pass through while acting like a drum to allow acoustic signals to pass through. In some embodiments, protective material 216 and/or protective material 218 are acoustically transmissive liquid blocking materials. In some embodiments, protective material 216 and/or protective material 218 are optional.

In an alternative embodiment, rather than utilizing a separate transmitter and a separate receiver, a transceiver that acts as both a receiver and transmitter is utilized. For example, receiver 214 is not utilized and transmitter 204 is a transceiver (e.g., piezoelectric transceiver).

Figure 3A:
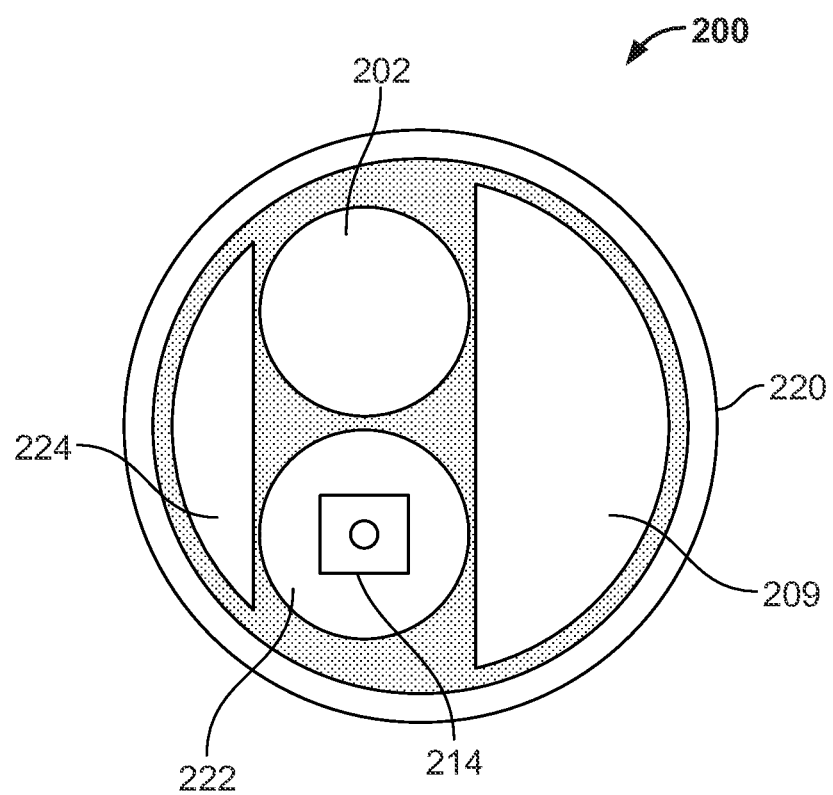
FIGS. 3A-3B are bottom view diagrams illustrating embodiments of a fill level sensor.
Figure 3B:
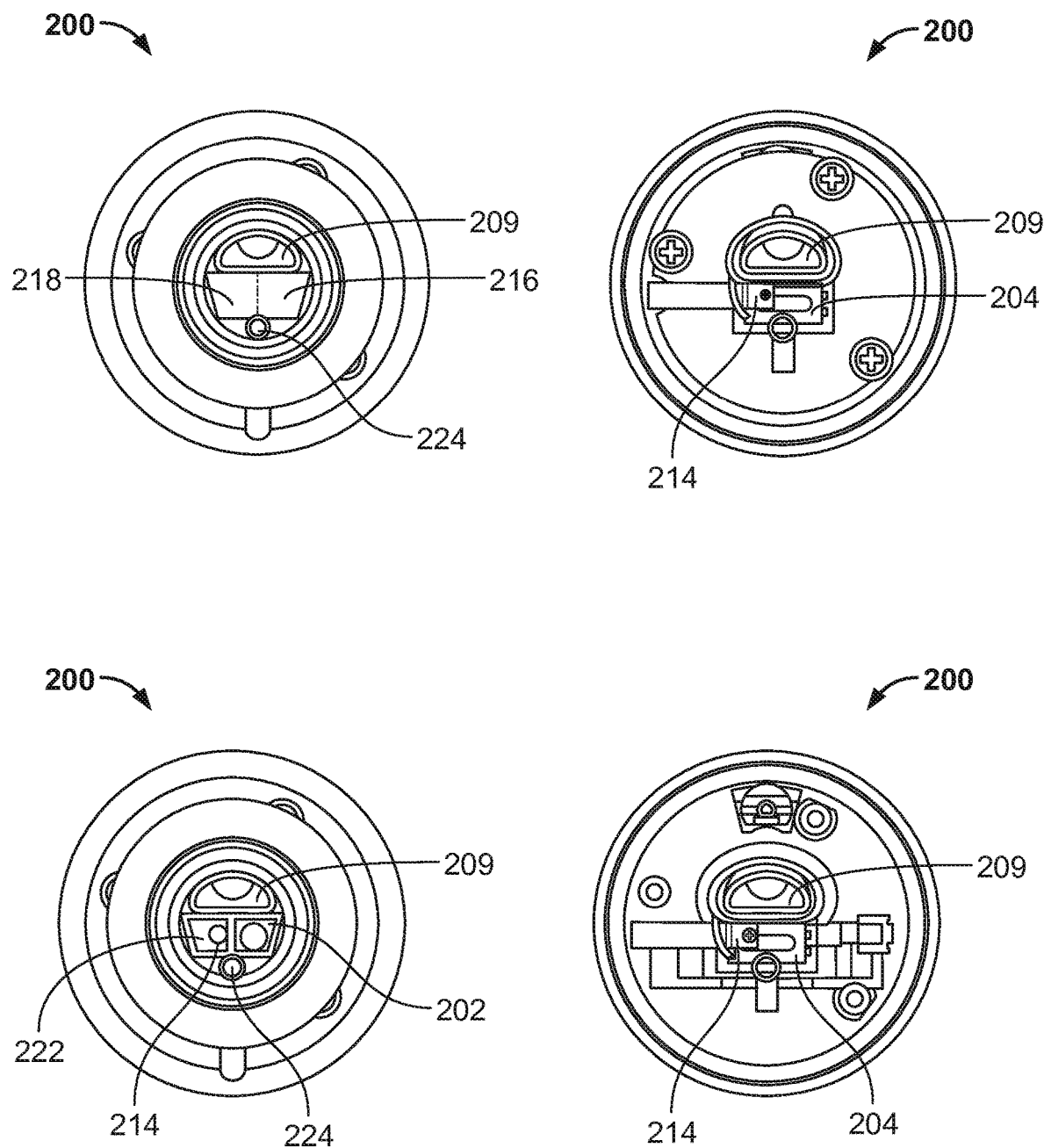

FIGS. 3A-3B are bottom view diagrams illustrating embodiments of a fill level sensor. Sensor 200 is sensor 200 of FIG. 2A or 2B. Sensor 200 includes flexible ridges 220 (e.g., rubber rings) that allows sensor 200 to be coupled to and seal an opening of a container (e.g., as shown in FIG. 1 and FIG. 2A). Spout input opening 209 allows contents (e.g., liquid contents of a container capped by sensor 200) that enter through spout input opening 209 to be channeled and outputted through spout 208 (shown in FIG. 2A). The signal output end of waveguide 202 is shown in FIGS. 3A and 3B. Receiver 214 is recessed inside receiver chamber 222. In some embodiments, protective material 216 covers the shown output opening of waveguide 202 and is attached to the shown opening edges of waveguide 202. In some embodiments, protective material 218 covers the shown output opening of receiver chamber 222 and is attached to the shown opening edges of receiver chamber 222. Vent output opening 224 (e.g., opening of a vent pipe) allows air to enter a container capped by sensor 200 as contents of the container is poured out through spout input opening 209. In order to show the internal components of various embodiments of sensor 200, one or more components of sensor 200 are not shown in FIGS. 3A-3B.

Figure 4A:
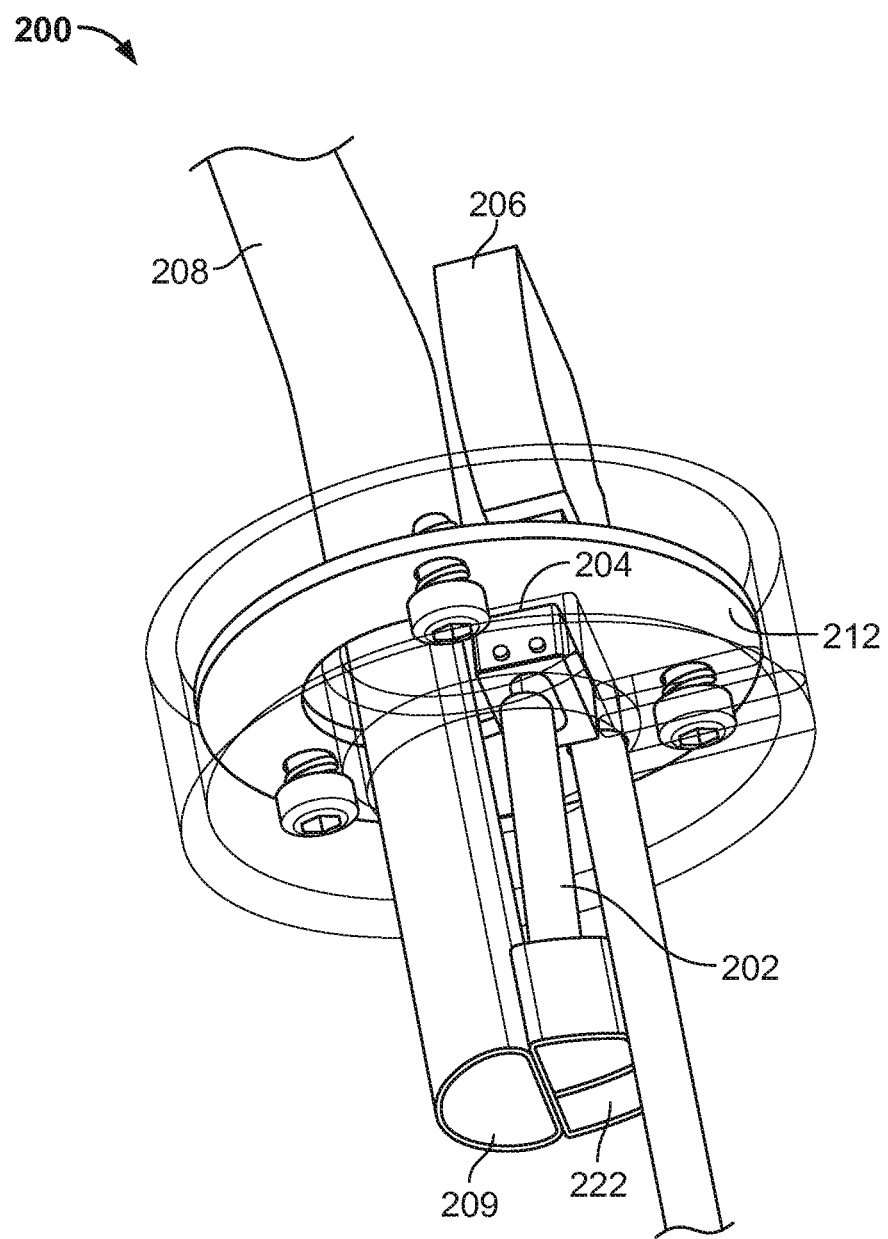
FIGS. 4A-4C are profile diagrams illustrating embodiments of a fill level sensor.
Figure 4B:
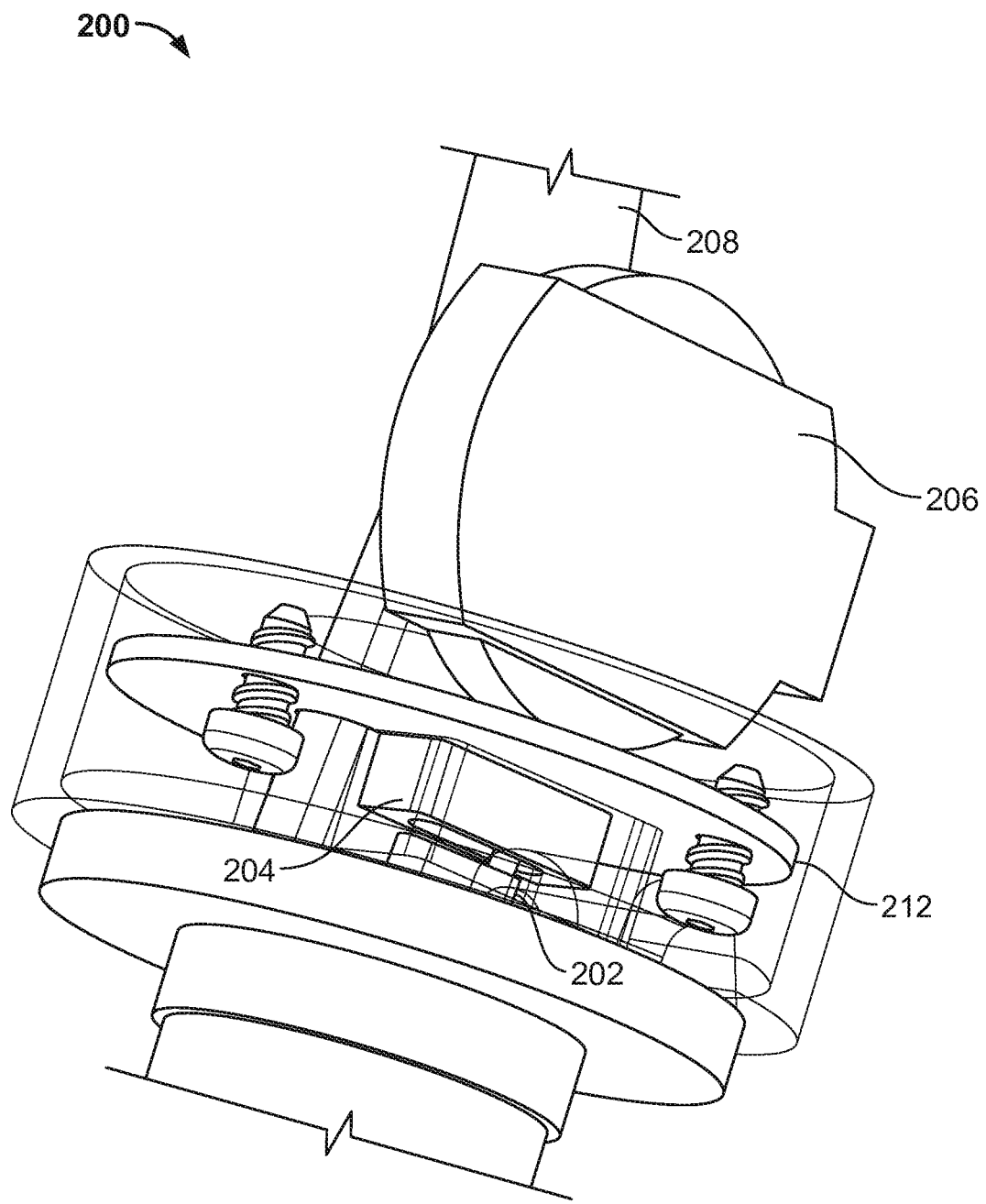
Figure 4C:
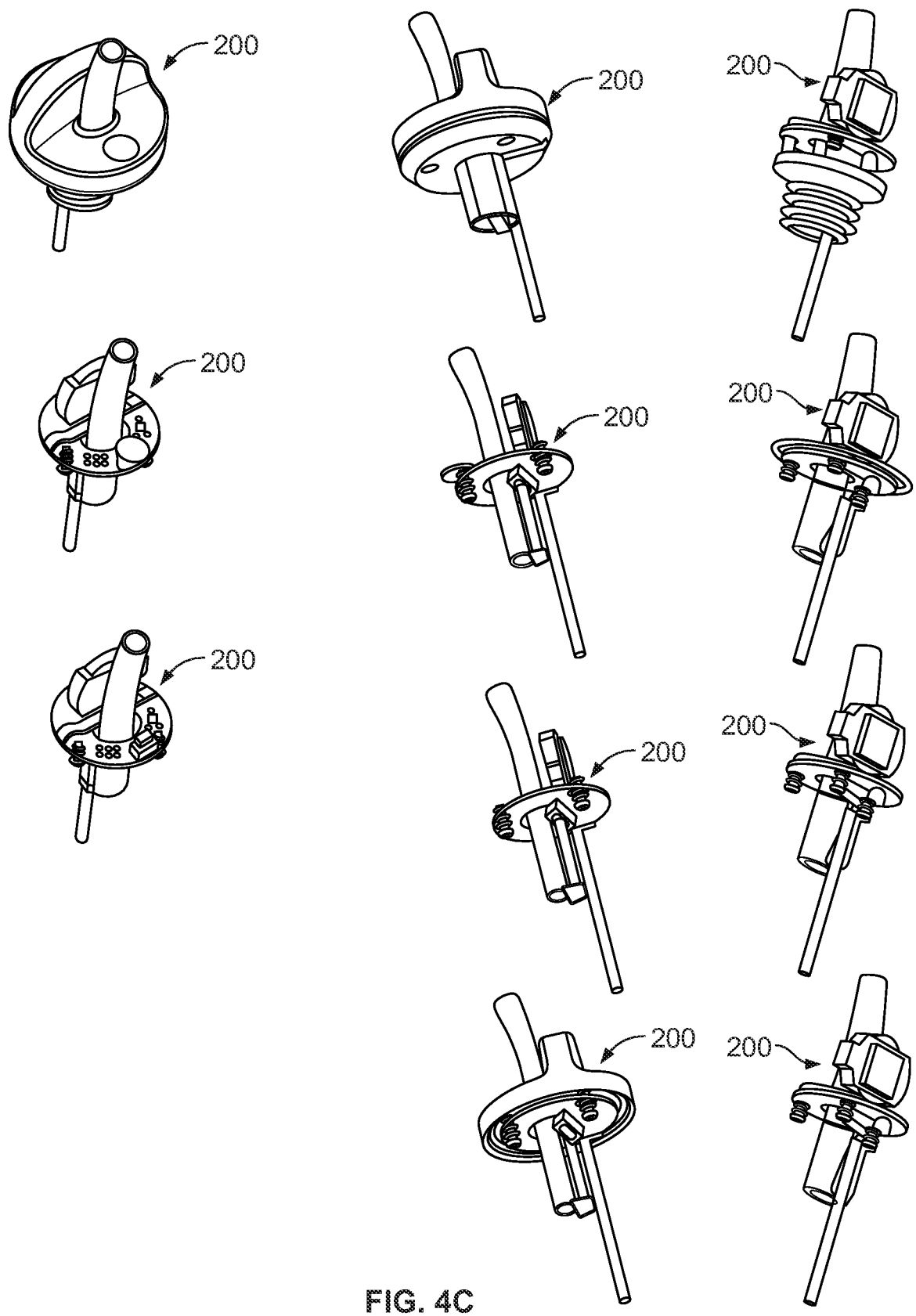

FIGS. 4A-4C are profile diagrams illustrating embodiments of a fill level sensor. The diagrams show various external and internal components of various embodiments of fill level sensor 200. In order to show the internal components of various embodiments of sensor 200, one or more components of sensor 200 are not shown in FIGS. 4A-4C.

Figure 5:
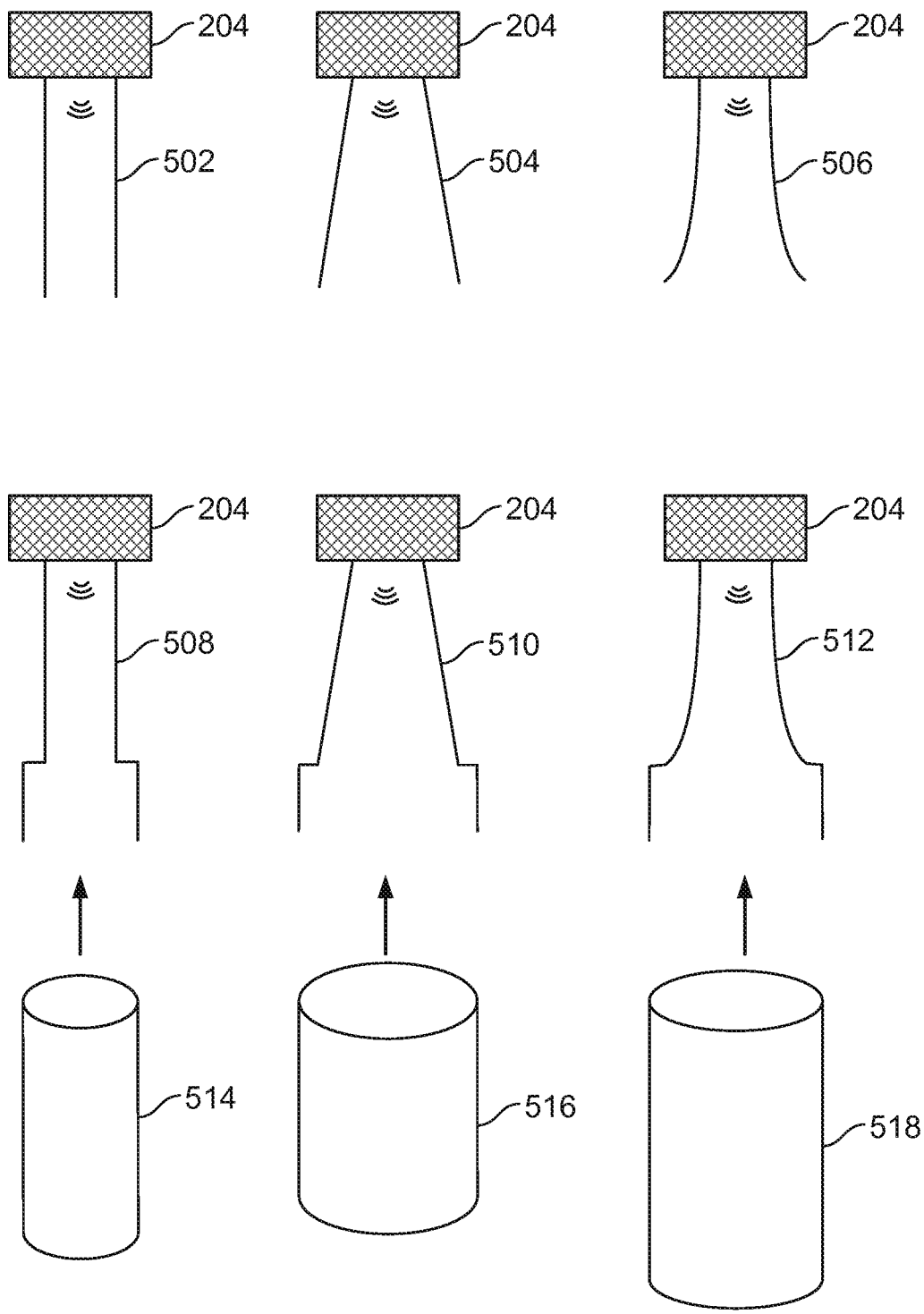
FIG. 5 is a diagram showing alternative embodiments of a waveguide.

FIG. 5 is a diagram showing alternative embodiments of a waveguide. In some embodiments, FIG. 5 shows alternative shapes of waveguide 202 shown in FIGS. 2, 3 and 4A.

Waveguides 502-512 show vertical cross-sectional diagrams of different embodiments of waveguide shapes. For example, although waveguides 502-512 are tubular in shape, the cross-sectional diagrams are shown to illustrate the hollow interior of the waveguides. Waveguide 502 includes substantially straight side walls that extend straight from the signal input end of waveguide 502 that receives signal input from transmitter 204 to the signal output end of waveguide 502. Waveguide 504 includes linearly sloped side walls that extend smoothly outward from signal input end of waveguide 504 that receives signal input from transmitter 204 to the signal output end of waveguide 504. Waveguide 506 includes exponentially sloped side walls that extend smoothly outward from the signal input end of waveguide 506 that receives signal input from transmitter 204 to the signal output end of waveguide 506.

In some embodiments, the output end of a waveguide is configured to accommodate a waveguide extension tube (e.g., tube with two open ends). For example, for certain types of containers, it may be beneficial to guide a signal outputted by transmitter 204 further down in to the container to measure fill level. By utilizing a waveguide extension tube, a waveguide is able to extend beyond the sensor 200. By extending the waveguide further down the container, undesired reflection in the container may be minimized. In some embodiments, the output end of the waveguide is enlarged to accommodate coupling with a waveguide extension tube. For example, in order to minimize the impedance mismatch between the output end of a waveguide with the input end of the waveguide extension tube to be coupled, the transition between the interior output opening of the sensor waveguide and interior input opening of the extension tube must be smooth. In some embodiments, the interior opening widths of waveguide extension tubes 514, 516 and 518 are substantially similar to interior opening widths of waveguides 508, 510, and 512, respectively.

Waveguide extension tubes 514, 516 and 518 are shown in profile view. Although waveguide extension tubes 514, 516 and 518 are shown separated from waveguides 508, 510, and 512, respectively, to show the different components, waveguide extension tubes 514, 516 and 518 may be inserted into waveguides 508, 510, and 512, respectively, to be coupled (e.g., friction coupling, mechanical coupling, etc.) together. To accommodate for the thickness of the waveguide extension tube, waveguides 508, 510, and 512 include bell shaped ends that can be coupled with waveguide extension tubes 514, 516, and 518, respectively to create a relatively smooth transition between the interior walls of the sensor waveguides and the waveguide extension tubes. In some embodiments, a waveguide extension tube is removable from a sensor waveguide. In some embodiments, a waveguide extension tube is permanently coupled (e.g., glued) to a sensor waveguide. Examples of the materials that make up waveguide extension tubes 514, 516, and 518 include a food grade polymer, plastic, rubber, stainless steel, and other metals.

Figure 6:
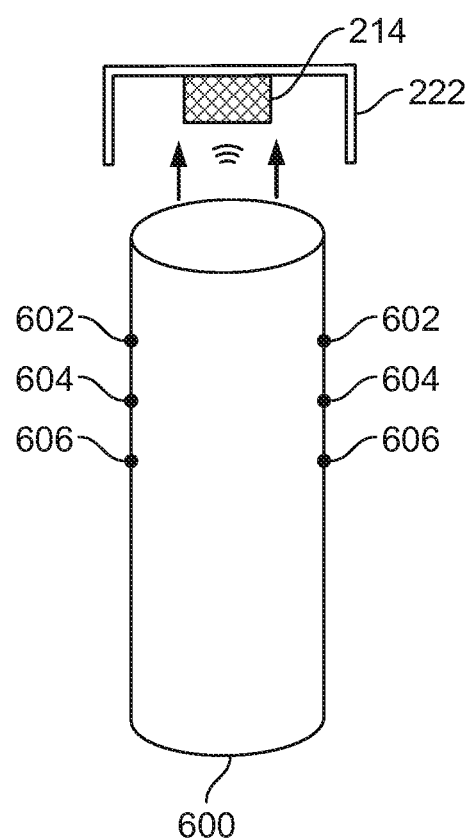
FIG. 6 is a diagram showing a receiver extension tube.

FIG. 6 is a diagram showing a receiver extension tube. In some embodiments, FIG. 6 shows an embodiment of receiver 214 and receiver chamber 222 of sensor 200 shown in FIGS. 2 and 3. Receiver 214 and receiver chamber 222 are shown in cross sectional view and receiver extension tube 600 is shown in profile view. Although receiver extension tube 600 is shown separated from receiver chamber 222 to show the different components, receiver extension tube 600 may be inserted into receiver chamber 222 to be coupled together. By utilizing a receiver extension tube, a receiver chamber is able to extend beyond the sensor 200.

In some embodiments, the output end of receiver chamber 222 is configured to accommodate receiver extension tube 600 (e.g., tube with at least two open ends). For example, for certain types of containers, it may be beneficial to receive a signal outputted by transmitter 204 further down in to the container within receiver extension tube 600. By extending further down the container the receiver chamber that will guide a received signal to receiver 214, undesired reflection in the container may be rejected from entering the extended receiver chamber. Receiver chamber 222 is configured to accommodate coupling (e.g., friction coupling, mechanical coupling, etc.) with receiver extension tube 600. The size of receiver chamber 222 is large enough to accommodate for the thickness of receiver extension tube 600. In some embodiments, a receiver extension tube is removable from receiver chamber 222. In some embodiments, receiver extension tube 600 is permanently coupled (e.g., glued) to receiver chamber 222. In some embodiments, at least one end of receiver extension tube 600 is sealed with an acoustically transmissive liquid blocking material (e.g., material 218 of FIG. 2A of FIG. 3B). The lengths, widths, and/or shape of receiver extension tube 600 may vary across different embodiments. Examples of the materials that make up receiver extension tube 600 include a food grade polymer, plastic, rubber, stainless steel, and other metals. In some embodiments, the interior opening width of receiver extension tube 600 is at least as large as a size of an opening of receiver 214 that is configured to receive a signal.

In the example shown, receiver extension tube 600 includes optional pairs of holes/slots 602, 604, and 606. Each hole of each pair is on the same horizontal axis position (e.g., vertical position) substantially opposite one another on receiver extension tube 600. Although three pairs have been shown, any number of pairs may exist in other embodiments. In some embodiments, pairs of holes/slots 602, 604, and 606 allow receiver 214 to act as a shotgun/parabolic microphone. For example, receiver 214 is able to directionally better detect signals received at the bottom of receiver extension tube 600 rather than the sides of extension tube 600. Signals received at the sides of receiver extension tube 600 (e.g., received through holes/slots 602, 604, and 606) may be largely cancelled out (e.g., signal waves are cancelled as signal is received through each opposite hole/slot of each hole/slot pair). In some embodiments, pairs of holes/slots 602, 604, and 606 are sealed with an acoustically transmissive liquid blocking material (e.g., material 218 of FIG. 2A and FIG. 3B).

Figure 7A:
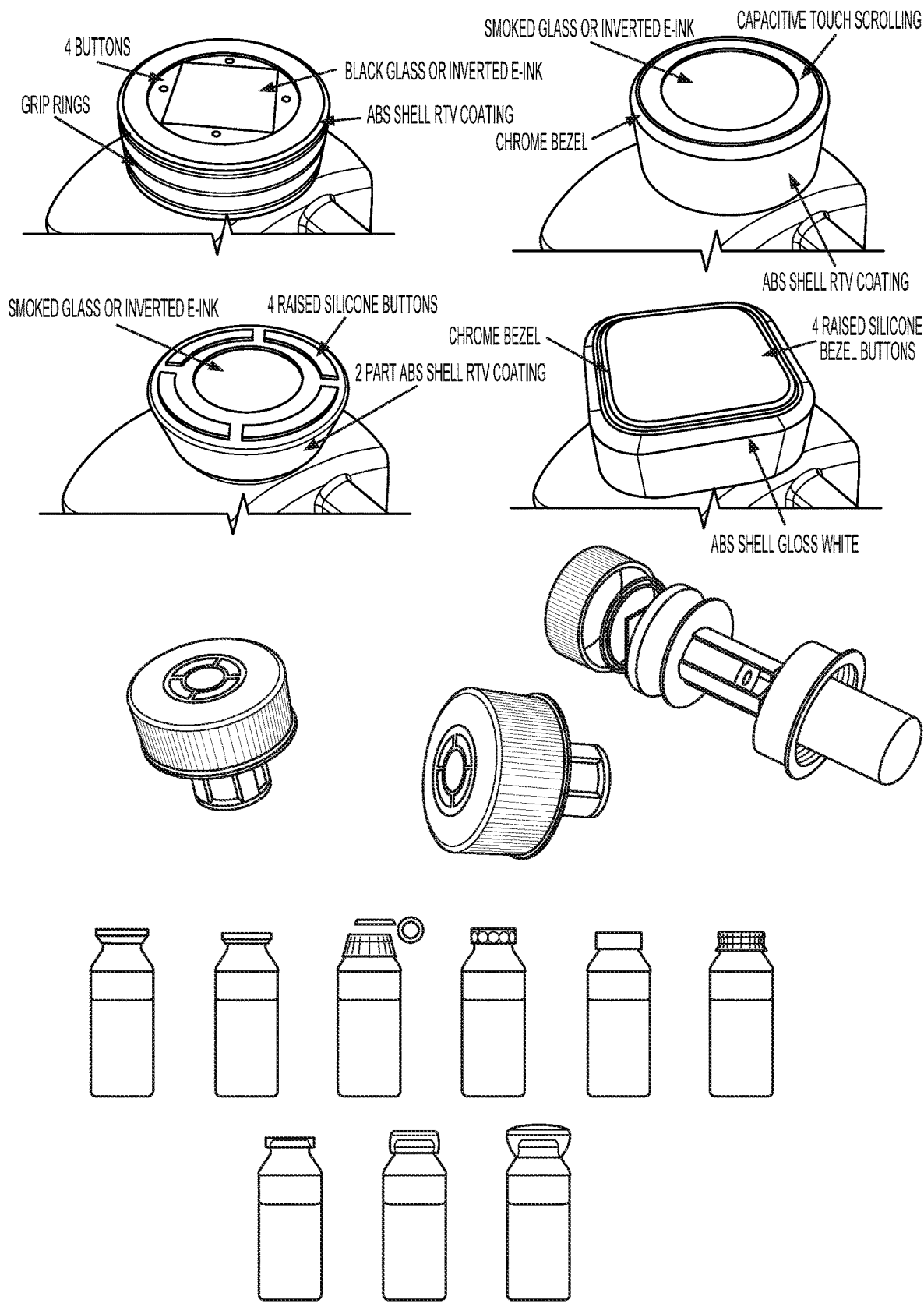
FIGS. 7A-7C show various container covers that may be similarly configured to include one or more of the components shown in other figures.
Figure 7B:
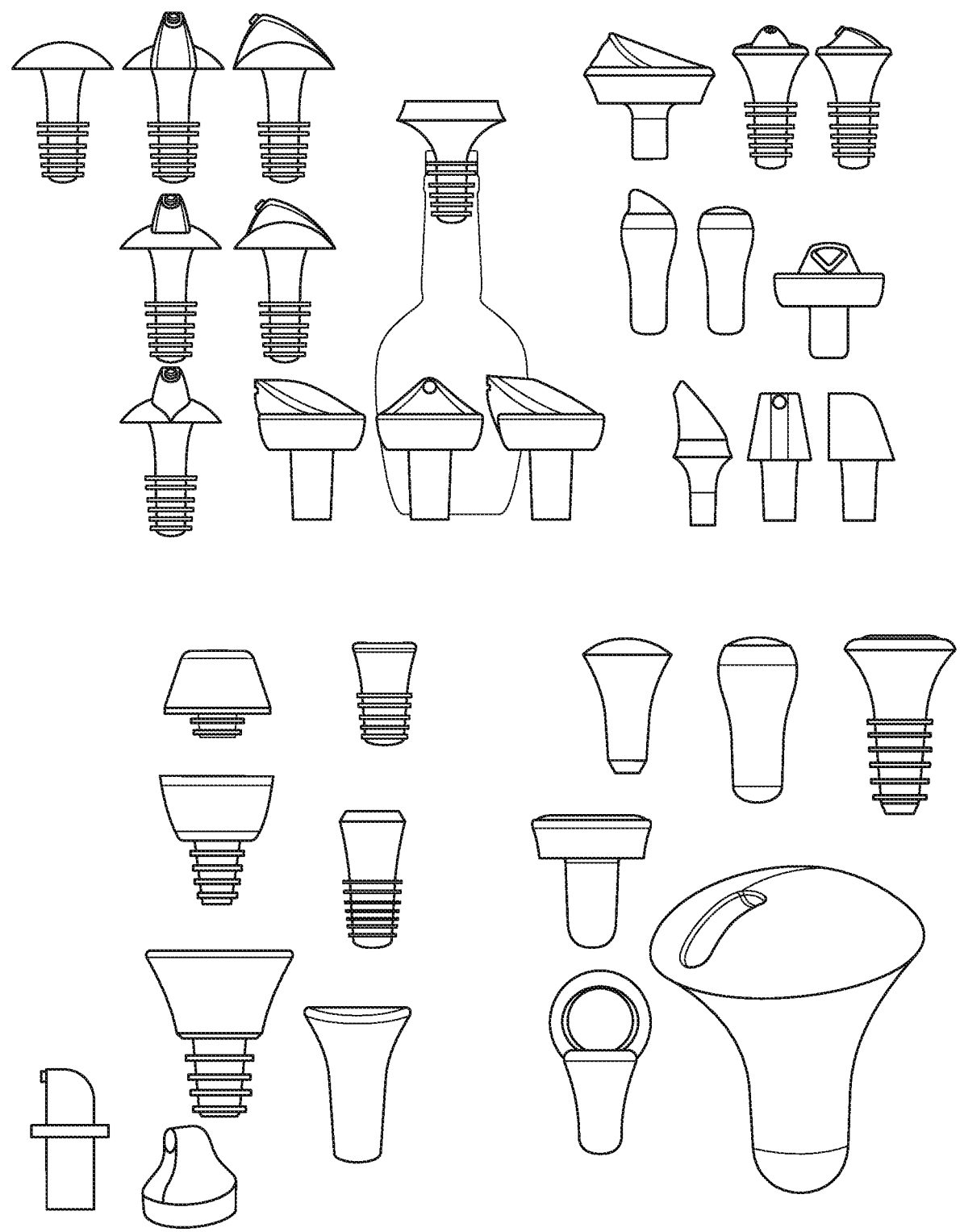
Figure 7C:
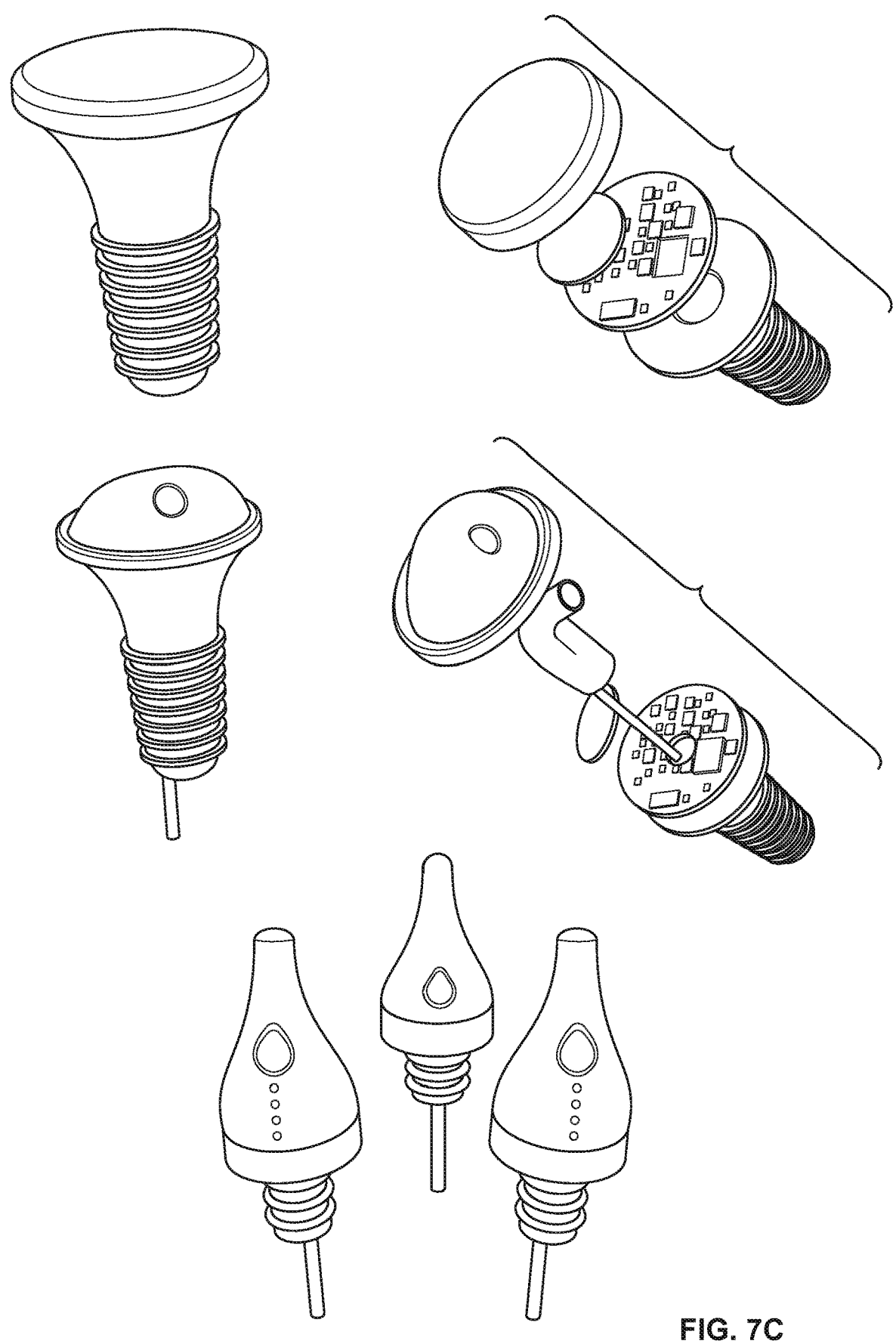

The example container cap shape of fill level sensors (e.g., sensor 200) shown in the Figures are merely illustrative. One or more of the internal components shown in FIGS. 2-6 may be configured and included similarly in different types of container covers/caps. FIGS. 7A-7C show various container covers that may be similarly configured to include one or more of the components shown in other figures.

Figure 8:
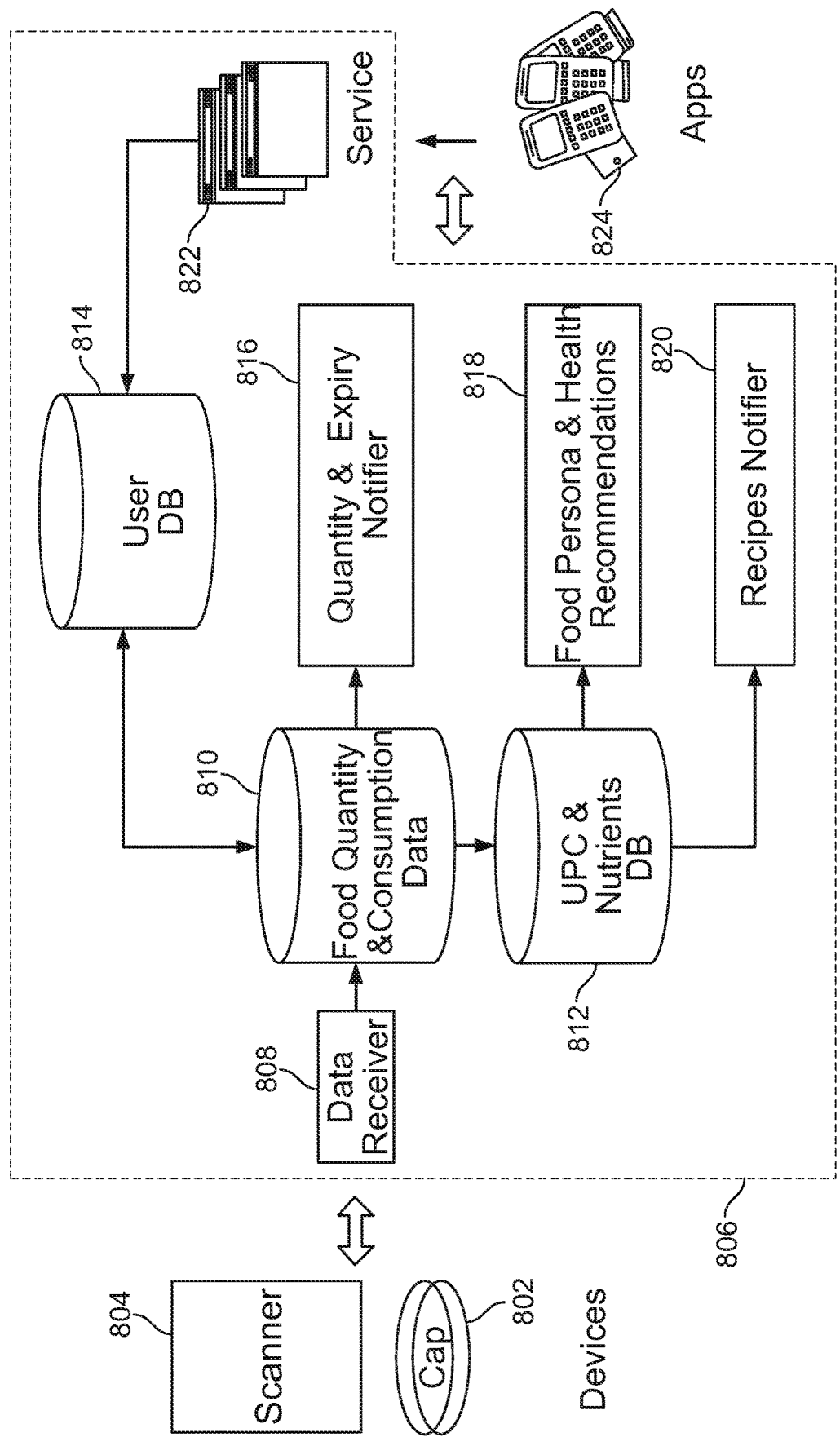
FIG. 8 is a system diagram illustrating components of an example food management ecosystem.

FIG. 8 is a system diagram illustrating components of an example food management ecosystem. Container cover 802 and receipt scanner 804 provides data to analysis system 806. For example, data is provided to analysis system via a wireless connection. Analysis system 806 includes data receiver 808, food quantity and consumption data storage 810, UPC and nutrients database 812, user data database 814, quantity and expiry notification component 816, food persona and health recommendations component 818, recipes notification component 820 and service interface 822. Applications of user devices 824 may access services provided by analysis system 806 via service interface 822. In some embodiments, container cover 802 includes sensor 100 and/or sensor 200 in FIGS. 1-7

Figure 9:
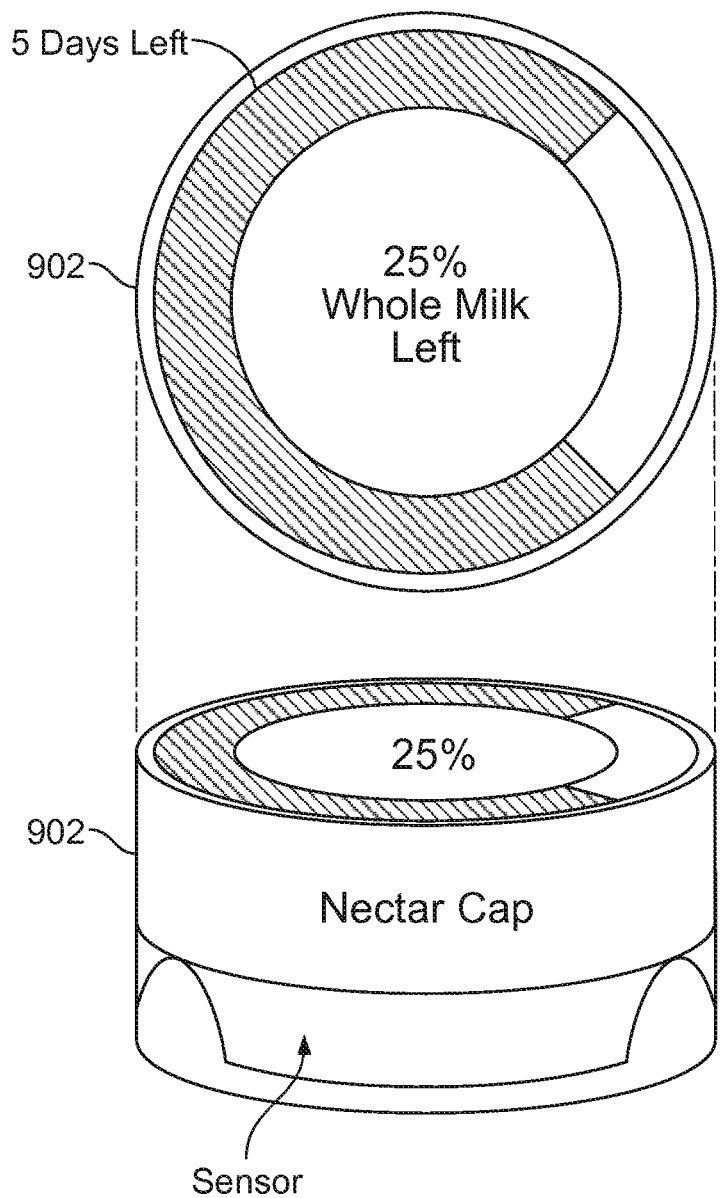
FIG. 9 is a diagram illustrating an embodiment of a container cover.

FIG. 9 is a diagram illustrating an embodiment of a container cover. Container cover 902 includes a display and one or more sensors configured to determine one or more properties of content included in a container covered by container cover 902. In some embodiments, container cover 802 of FIG. 1 is container cover 902 of FIG. 9. In some embodiments, container cover 902 is sensor 100 and/or sensor 200 in FIGS. 1-7.

An example of container cover 902 includes a cap of a beverage container. In some embodiments, container cover 902 may measure the quantity of food item contained, take inputs for the expiration date, measure the chemical nature and nutrient value of the food contents and transmit these data (e.g., including unique identifier associated with container cover) wirelessly to an analysis system (e.g., system 806 of FIG. 8) via a network cloud. All shapes, sizes and volume are included under the definition of the container cover. For example, cereal box containers enclosures and wine bottle stoppers are example container covers. Spouts and pourers combined with stoppers for beverage bottles are examples of container covers. Examples of a container include cereal containers, food storage jars, boxes, tupperware, ceramic jugs, and any container that can be at least partially covered with the container cover. In some embodiments, a container cover for a baby bottle detects the quantity, quality and temperature, while also measuring the amount of baby food formula being consumed.

In some embodiments, the analysis system in turn identifies the container cover's unique ID and associates the measured quantities to the consumer who has been associated with the container cover through the analysis and tracking service. In various embodiments, the container cover is configured to provide/include one or more of the following (e.g., a processor is configured to carry out or coordinate one or more of the following):

- Detect quantity and communicates to the consumer.
- Ultrasound, piezo-resistive, inductive, capacitive, IR, line, and video sensors for quantity detection.
- Ultrasound, piezo-resistive, inductive, capacitive, IR, line, and video sensors that could sense the flow out a cap and measure volume of flow.
- Detects expiry either through user input or by sensing the chemical composition and nutrient value of the food using humidity, barometric, light, pH, and odor sensors.
- Take inputs regarding the classification of the food type (e.g., 1% milk, whole milk, Soy Milk; pulp, no pulp orange juice, etc.).
- Temperature sensor and notifies the consumer if the temperature is not optimal for storage (e.g., 20 F to 60 F).
- Click wheel input mechanism built into the cap based on mechanical and electrical components (e.g., capacitive sensor).
- Display that shows the quantity, expiration date, type of product, nutrient information, temperature and last used information.
- Ability to identify and connect to a local wireless network or Bluetooth network.
- Ability to detect motion using an accelerometer so it can turn on/off on a need basis to optimize power consumption.
- An optimal power management algorithm to store, manage, and transmit the information back and forth with the analysis system without draining the power rapidly.
- A mechanical fixture that allows the container cover to measure the quantity while enclosed in a casing that insulates and protects the electrical system from food and beverages.
- A module that is corrosion resistant and can operate in temperatures from −40 F to 115 F.
- Ability to store and transmit only when the network connectivity is available.
- Ability to associate information with unique consumer identity.
- A touch sensitive screen based on but not limited to resistor or capacitive sensor mechanism which allows for one touch reordering (e.g., the screen could be either included in the container cover or could be separate from the container cover).
- Structure that helps contain solid, liquids, and gases within a container (e.g., variations of container cover shapes and structures could include but not limited to circular, square, rectangular, and any polygon shape).
- Sensor module.
- Pourer or spouts could be combined into single unit or the pourer/spout could be independent of the sensors and processor module.
- Impellers, flow restrictive mechanisms and any additional conduits that attach to the cap and can be attached with a sensor.

Figure 10:
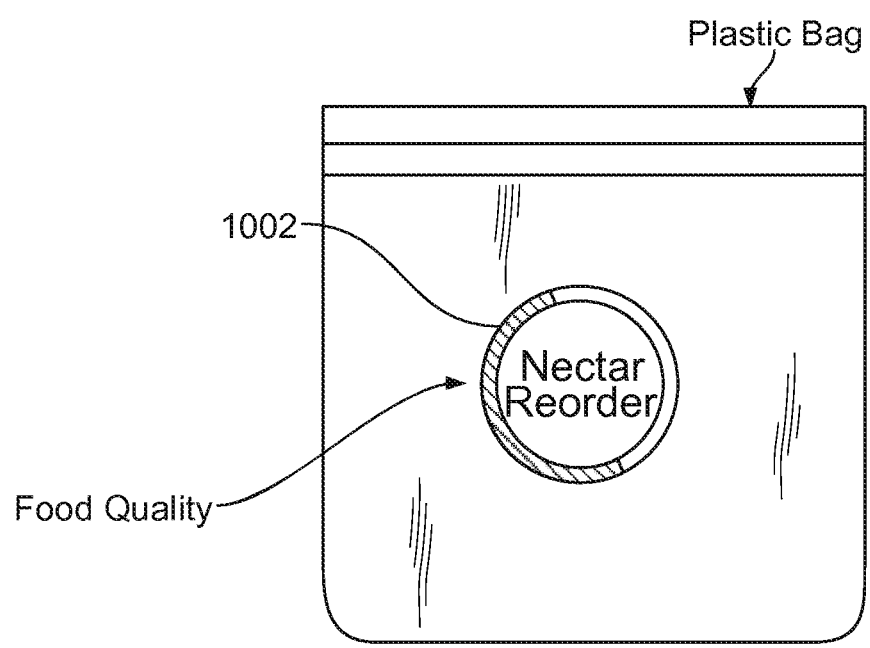
FIG. 10 is a diagram illustrating an embodiment of a patch of a container.

FIG. 10 is a diagram illustrating an embodiment of a patch of a container. In some embodiments, container cover 802 of FIG. 8 is container patch 1002. In some embodiments, container patch 1002 is sensor 100 and/or sensor 200 in FIGS. 1-7. Patch 1002 as shown may be made with various sensors that can help measure the quantity of food item contained, take inputs for the expiration date, measure the chemical nature and nutrient value of the food contents and transmit these data (e.g., including unique identifier associated with container cover) wirelessly to an analysis system (e.g., system 106 of FIG. 1) via a network cloud. Patch 1002 may be applied to a bag container. Various forms of the patch include markers, stickers, clips, tie threads, and locks (e.g., zip lock mechanism with sensors). Variations of the patch/marker shapes and structures could include but not limited to circular, square, rectangular, and any polygon shape. All shapes, sizes and volume are included under the definition of patches/markers.

In some embodiments, the analysis system in turn identifies the container patch's unique ID and associates the measured quantities to the consumer who had been associated with the patch through the analysis and tracking service. In various embodiments, the patch is configured to provide/include one or more of the following (e.g., a processor is configured to carry out or coordinate one or more of the following):

- Ultrasound, inductive, humidity, and pH sensors utilized to measure quantity and freshness of food stored.
- A display that shows the quantity, expiration date, type of product, nutrient information, temperature and last used information.
- Ability to identify and connect to a local wireless network or Bluetooth network.
- Ability to detect motion using an accelerometer so it can turn on/off on a need basis to optimize power consumption.
- An optimal power management algorithm to store, manage, and transmit the information back and forth with the analysis system without draining the power rapidly.
- A mechanical fixture that allows for the patch to measure the quantity while enclosed in a casing that insulates and protects the electrical system from the contents in the bag.
- A module that is corrosion resistant and can operate in temperatures from −40 F to 115 F.
- Ability to store and transmit only when the network connectivity is available.
- Ability to associate information with unique consumer identity.
- A touch sensitive screen based on but not limited to resistor or capacitive sensor mechanism which allows for one touch reordering.

Figure 11:
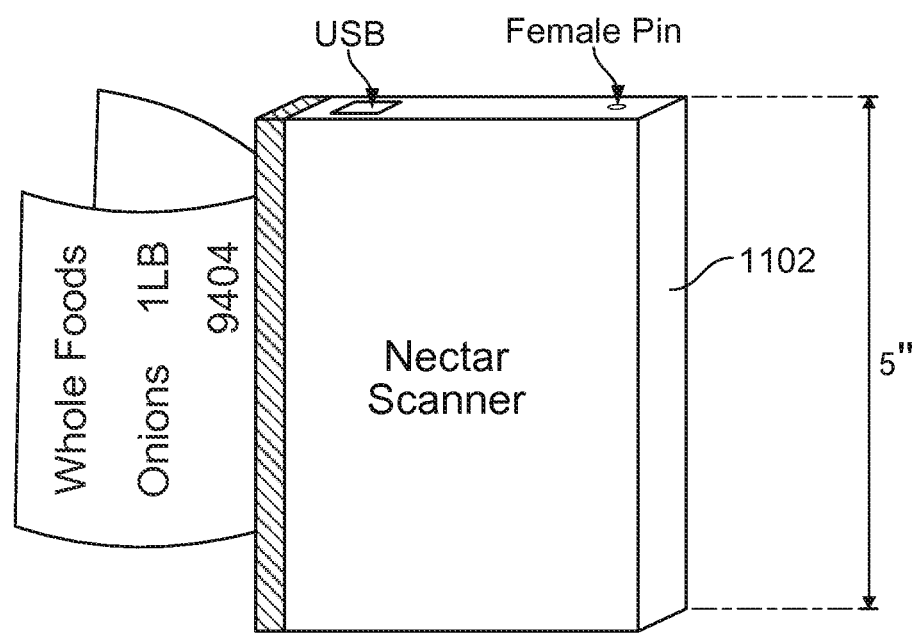
FIG. 11 is a diagram illustrating an embodiment of a receipt scanner.

FIG. 11 is a diagram illustrating an embodiment of a receipt scanner. In some embodiments, scanner 804 of FIG. 8 is scanner 1102. Receipt scanner 1102 scans receipts such as grocery store receipts.

For example, a consumer can insert receipts into scanner 1102 and scanner 1102 obtains an image of the receipt to determine each item listed as purchased on the receipt. Scanner 1102 includes a stepper motor that is operated synchronously with a line sensor or camera for taking an optimal amount of pictures. The scanned data may be transmitted wirelessly to an analysis system via a network cloud and a unique identifier of the scanner 1102 identifies the data. The analysis system in turn identifies the scanner's unique ID and associates the purchased items and quantities to the consumer associated with the scanner.

In various embodiments, the scanner is configured to provide/include one or more of the following (e.g., a processor is configured to carry out or coordinate one or more of the following):

- A receipt sized input mechanism that uniformly moves the receipt for scanning each item data—including name, price, quantity and item UPC code.
- A mechanism to scan using a combination of stepper motor and imaging line sensors.
- The speed of moving the stepper motor to match the camera speed for an optimal number of images.
- Camera position, angle, and distance from the scan area that offers an optimal picture of each scanned area.
- Ability to identify and connect to a local wireless network for transmitting receipt information.
- Ability to store and transmit receipt information only when the network connectivity is available.
- Ability to associate the receipt information with unique consumer identity.

Reordering

In some embodiments, an analysis system listens to all devices and collects data inputs (e.g., shown in FIG. 8). Each container cover/patch and/or receipt scanner or any other device may be each uniquely identified by a hardware identification number (ID). This identifier may be associated with a particular consumer (e.g., the ID could be transferred and associated with a new consumer). The data inputs from a container cover/patch may be associated with device ID and stored under the corresponding consumer profile. The "data" includes but not limited to—food item name, UPC, quantity, price, store it was bought from, date and time of purchase, servings per use, time of servings consumed, location, expiration, chemical composition, odor, color, temperature, ingredients used, and various nutrient amounts (e.g., carbohydrates, proteins, fats, sugars). Once sufficient samples are collected over a reasonable time (e.g., at least a few hundred) the analysis system may start to "learn" the following patterns and habits including but not limited to: amount of food needed by the consumer, consumable state, and the time when the food item needs to be reordered and replenished.

Based on the consumption patterns and learning, the analysis system may notify the consumer about running out of a certain food item or warn about expiration of food. In response to the notifications the user may be provided an option to order the food item.

In various embodiments, the analysis system is configured to provide/include one or more of the following:

- Store food related "data" that offers a view into food consumption patterns by a consumer: food item name, UPC, quantity, price, store it was bought from, date and time of purchase, servings per use, time of servings consumed, location, expiration, chemical composition, odor, color, temperature, ingredients used, and various nutrient amounts (e.g., carbohydrates, proteins, fats, sugars).
- A mechanism to uniquely associate various devices that help collect food data with each consumer.
- The ability to listen, collect and store millions of devices at any given point in time.
- Algorithm that mines, learns, and predicts amount of food needed by the consumer and consumable state of the food item (expiration dates).
- Ability to notify the user to reorder the necessary food and beverages or automatically reorder and replenish Recommendations to Improve Health In some embodiments, an analysis system offers nutritional facts associated with each food item. This may be provided using a UPC and nutritional facts database or an existing databases with similar information. Using such UPC and nutrition database each consumer's food consumption pattern may be summarized by tracking various nutritional information over a specified time period (e.g., 500 grams of sugar per week, 300 grams of proteins per month, 20 gram of trans fat, etc.). Based on the quantitative profiling of food consumption, a "food persona" may be determined. This analysis may be provided to consumers to allow them to make informed choices around consuming certain food and beverages. The analysis may be utilized to ascertain healthy nutrient levels and a user may be notified of over consumption or deficiency of a certain nutrient for optimal health.

Consumers may integrate and connect the aggregated data collected from wearable devices such as FitBit, Jawbone etc. to the analysis system. Combined with the fitness data from various wearable devices, the analysis system may also suggest which nutrients/food and beverages might be a cause for degradation or improvement of health. The analysis system may offer a mechanism for consumers to provide allergy and other ailment information. The analysis system may then check various food and beverages being ordered and consumed that could result in allergy and medical issues and warn the user of the possible harm or potential upside.

In some embodiments, a user's social graph is obtained from social networks such as Facebook (upon obtaining permission from the user) and associated with the food persona built by the analysis system. Based on food persona which offers insights into the consumer interests and consumption of various foods, the analysis system may utilize connected friends of the network to identify food consumption recommendations. Based on the food persona, the analysis system may mine for similar personas and recommend beneficial food and beverages, determine suggested inventory (e.g., shopping lists), suggest consumption patterns, and suggest recipes. By connecting users based on food persona, a graph of users based on food persona called "food graph" may be determined. Such a network of consumers based on food persona may form a community to allow discussion of various health benefits. Famers, food brands, and chefs etc. may then recommend food and beverages that match certain food persona.

In various embodiments, the analysis engine is configured to implement/include one or more of the following:

- Devices that track food consumption patterns and habits to compute nutritional intake per period (minute/day/week/month).
- Each consumer is associated with various foods and their nutritional impact on them—there by developing a unique profile—"Food Persona."

Aggregate health data from various fitness devices for a given consumer, compare it with the food intake data collected from the devices such as the container cover and the receipt scanner, and make recommendations on various types of nutrients and food intake.

Take inputs from a consumer regarding allergies and special needs related to food, compare it with the food intake data collected from the devices such as the container cover and the receipt scanner and notify/warn users about possible issues with certain food they have purchased, ordered or may order.

Identify food personas that have similarity and connecting them to form a consumer graph called "Food Graph".

Ability to target food and beverages, recipes and nutritional education from brands, farmers, chefs and educators based on food persona.

Recipe Recommendations

A recipe for a prepared meal may be based on various factors: availability of food and beverages, season, age, dietary requirements, ethnicity, holidays, social recommendations etc. In some embodiments, a Recipe Recommendation service analyzes availability of food and beverages in real time, checks the seasons, suggestions from friends and will recommend the user the best possible recipes to cook (e.g., shown in FIG. 8). Alongside the recipe recommendations, notifications for ordering missing food and beverages may be also sent to the user.

In various embodiments, the analysis system is configured to provided/include one or more of the following:

Real time recipe recommendation based on availability of food and beverages owned by the consumer, dietary restrictions, age, season, ethnicity, holidays, social recommendations.

Notifications for ordering/re-ordering food and beverages that might be missing to cook a specific recipe so it's delivered on time for cooking (as specified by the user)

One Tap Reordering

Figure 12:
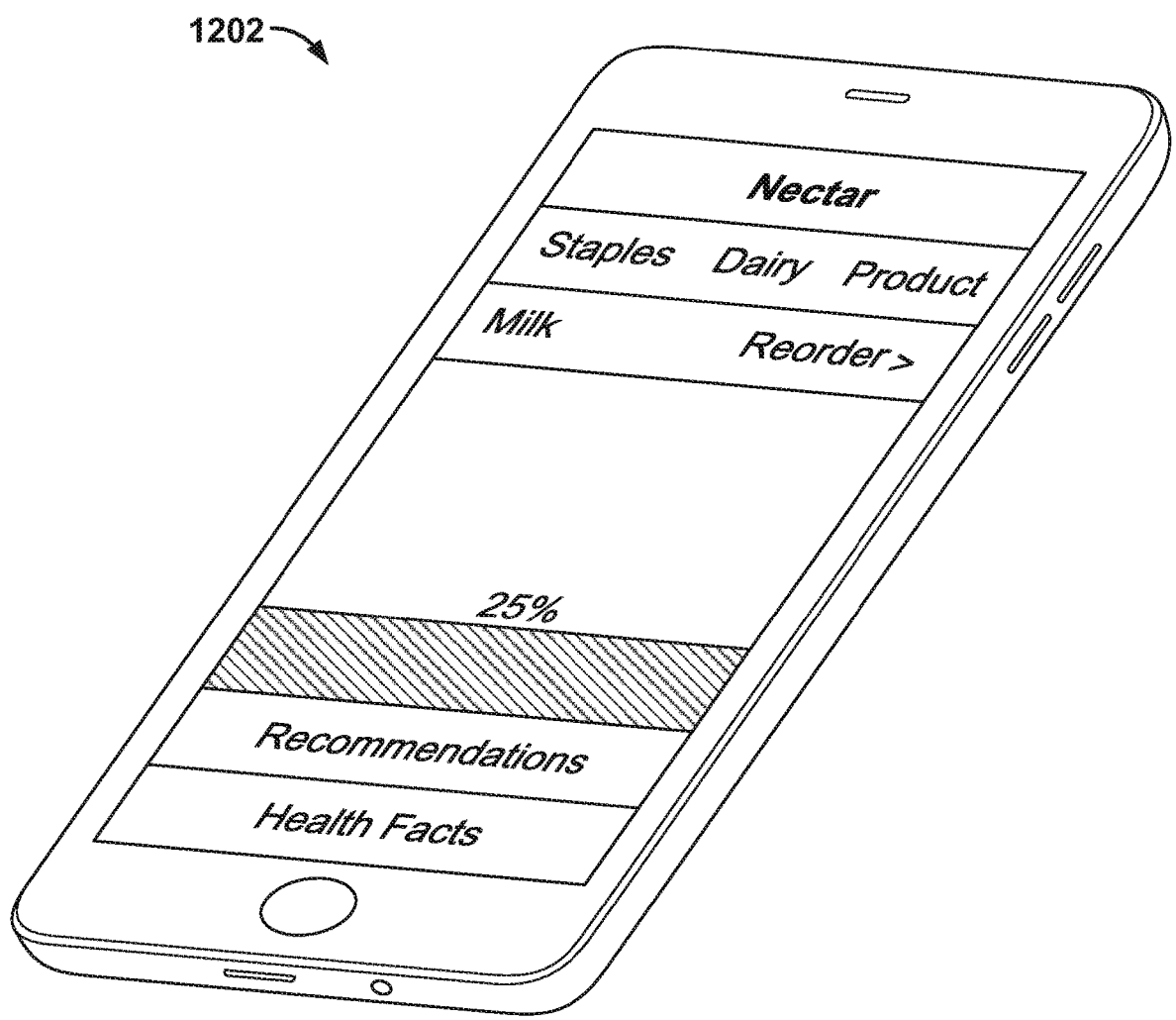
FIG. 12 is a diagram illustrating an embodiment of a mobile application interface.

FIG. 12 is a diagram illustrating an embodiment of a mobile application interface. In some embodiments, user device 824 of FIG. 8 includes a mobile device configured to provide interface 1202. In some embodiments, a mobile application (e.g., application of user device 824 of FIG. 8) to queries for information related to the consumer. The application may then display the food availability, various notifications such as reordering, health improvements, recipe recommendations and food persona (e.g., nutrient analytics) of the consumer.

When a user gets a notification to re-order a certain food item the user may tap on the notification and the food would be automatically delivered to their preferred physical address from their preferred source without any further action or steps from the consumer. This "One Tap Re-ordering" may be indicated via interface 1202. The "One Tap Re-ordering" may be made possible by aggregating several fragmented services in a unique manner. When the user downloads the mobile application or subscribes to the food analysis and tracking services, user preferences on delivery address, payments, and preferred time of delivery may be received and stored. Various delivery service options (e.g., Amazon Fresh, Google Shopping Express, Instakart, other food marketplace, local farmers, etc.) may be aggregated. A consumer's preference for the delivery service may be stored alongside payment, delivery location and delivery time preferences. In some embodiments, once the reorder notification is indicated, a one or more of services are initiated in the background and the food is delivered at the time and location as specified without any further action from the consumer.

In various embodiments, the mobile application is utilized to provide one tap food reordering that helps users get the food delivered to their preferred location and preferred time without any further action. In some embodiments, the mobile application provides access to a delivery services marketplace that offers the user a choice of choose from a host of delivery services.

Reminder for Pickup Based on Location

In some embodiments, the analysis system tracks food content owned by a user. In some embodiments, a mobile application tracks the current location of the user using the GPS locations provided by a mobile device (e.g., Smartphone, Tablet, wearable computer, etc.). The information of whether a certain food item is running low or about to expire and the current location of a user device are utilized to offer recommendation to pick those food and beverages when the user location is nearby a merchant that carries the food and beverage. In some embodiments, the mobile application locates a user's presence in or near a store and detects that the user is running low on a specific food item and notifies the user to pick up the food item while at the store.

The examples shown in the figures do not necessarily show every component of the embodiments shown. The figures have been simplified to illustrate the embodiments clearly. Other components not shown may be included in the embodiments. Any of the components shown in the figures may be optional. The figures have not been drawn to absolute and/or relative scale. The components shown may be of any relative or absolute dimension.

The methodology described here can be implemented on a computer system or network. A suitable computer system can include at least a processor and memory; optionally, a computer-readable medium that stores computer code for execution by the processor. Once the code is executed, the computer system carries out the described methodology.

In this regard, a "processor" is an electronic circuit that can execute computer programs. Suitable processors are exemplified by but are not limited to central processing units, microprocessors, graphics processing units, physics processing units, digital signal processors, network processors, front end processors, coprocessors, data processors and audio processors. The term "memory" encompasses an electrical device that stores data for retrieval. In one aspect, therefore, a suitable memory is a computer unit that preserves data and assists computation. More generally, suitable methods and devices for providing the requisite network data transmission are known.

Also contemplated is a non-transitory computer readable medium that includes executable code for carrying out the described methodology. In certain embodiments, the medium further contains data or databases for such methodology.

Embodiments can include program products comprising non-transitory machine-readable storage media for carrying or having machine-executable instructions or data structures stored thereon. Such machine-readable media may be any available media that may be accessed by a general purpose or special purpose computer or other machine with a processor. By way of example, such machine-readable storage media may comprise RAM, ROM, EPROM, EEPROM, CD-ROM or other optical disk storage, magnetic disk storage or other magnetic storage devices, or any other medium which may be used to store desired program code in the form of machine-executable instructions or data structures and which may be accessed by a general purpose or special purpose computer or other machine with a processor. Combinations of the above also come within the scope of "machine-readable media." Machine-executable instructions comprise, for example, instructions and data that cause a general purpose computer, special-purpose computer or special-purpose processing machine(s) to perform a certain function or group of functions.

Embodiments of the present disclosure have been described in the general context of method steps which may be implemented in one embodiment by a program product including machine-executable instructions, such as program code, for example in the form of program modules executed by machines in networked environments. Generally, program modules include routines, programs, logics, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

As previously indicated, embodiments of the present disclosure may be practiced in a networked environment using logical connections to one or more remote computers having processors. Those skilled in the art will appreciate that such network computing environments may encompass many types of computers, including personal computers, hand-held devices, multi-processor systems, microprocessor-based or programmable consumer electronics, network PCs, minicomputers, mainframe computers, and so on. Embodiments of the disclosure also may be practiced in distributed and cloud computing environments where tasks are performed by local and remote processing devices that are linked, by hardwired links, by wireless links or by a combination of hardwired or wireless links, through a communications network. In a distributed computing environment, program modules may be located in both local and remote memory storage devices.

Although the discussions above may refer to a specific order and composition of method steps, it is understood that the order of these steps may differ from what is described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present disclosure. Such variations will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed here. For example, the terms "comprising", "including," "containing," etc. shall be read expansively and without limitation. Additionally, the terms and expressions employed here have been used as terms of description and not of limitation; hence, the use of such terms and expressions does not evidence and intention to exclude any equivalents of the features shown and described or of portions thereof. Rather, it is recognized that various modifications are possible within the scope of the disclosure claimed.

By the same token, while the present disclosure has been specifically disclosed by preferred embodiments and optional features, the knowledgeable reader will apprehend modification, improvement and variation of the subject matter embodied here. These modifications, improvements and variations are considered within the scope of the disclosure.

Although the disclosure has been described in conjunction with the above-mentioned embodiments, the foregoing description and examples are intended to illustrate and not limit the scope of the disclosure. Other aspects, advantages and modifications within the scope of the disclosure will be apparent to those skilled in the art to which the disclosure pertains.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for quantity analysis, comprising:
 a communication interface configured to receive a quantity identification of an amount of content included in a consumable consumer product container, wherein:
   a container cover of the consumable consumer product container includes a transmitter configured to emit a signal into the consumable consumer product container using a waveguide;
   the transmitter is located inside one end of the waveguide;
   an acoustically transmissive liquid blocking material covers the transmitter;
   the acoustically transmissive liquid blocking material blocks the content in the container from coming in contact with the transmitter and allows the signal emitted by the transmitter to at least in part pass through the acoustically transmissive liquid blocking material;
   the container cover includes a receiver configured to be at least in part inside a neck of the consumable consumer product container when the container cover is engaged with the consumable consumer product container;
   the receiver is located in a receiver chamber;
   an opening of the receiver chamber is sealed by the acoustically transmissive liquid blocking material;
   the acoustically transmissive liquid blocking material covering the transmitter is in the same vertical location as the opening of the receiver chamber;
   the receiver is located inside one end of the receiver chamber;
   the receiver chamber is separate from the waveguide;
   the receiver is in a different vertical location as the transmitter;

the receiver is configured to receive a version of the signal emitted by the container cover;

the container cover is configured to determine the quantity identification including by determining a magnitude value associated with an amount of distance traveled by the emitted signal including by ignoring a portion of the received version of the emitted signal to at least in part ignore a coupling between the transmitter and the receiver and filtering at least a portion of the received version of the emitted signal to isolate a desired signal and detecting a signal peak in the isolated desired signal;

the container cover includes a battery and an accelerometer configured to detect a motion of the container cover; and the detected motion is utilized to optimize power consumed from the battery; and a processor coupled with the communication interface and configured to:

analyze the quantity identification along with a history of past quantity identifications received from the container cover over time to determine an analysis result; and perform an action associated with the content of the container based on the analysis result.

2. The system of claim 1, wherein the quantity identification is received wirelessly from the container cover.

3. The system of claim 1, wherein the quantity identification is received via a wireless signal from the container cover.

4. The system of claim 1, wherein the transmitter is included in a first enclosed space that is at least in part enclosed by the acoustically transmissive liquid blocking material, the container cover includes a receiver configured to receive the signal emitted by the transmitter and reflected within the container, the receiver is separate from the transmitter, and a second enclosed space is at least in part enclosed by the acoustically transmissive liquid blocking material that is ultrasonically transmissive.

5. The system of claim 1, wherein the container cover utilizes ultrasound to determine the quantity identification.

6. The system of claim 1, where in the container cover utilizes one or more of the following to determine the quantity identification: an inductive sensor, a capacitive sensor, a piezo-resistive sensor, a light sensor, and a video sensor.

7. The system of claim 1, wherein the container cover utilizes a video sensor to determine the quantity identification.

8. The system of claim 1, wherein the container cover detects a chemical composition of the content of the container.

9. The system of claim 1, wherein the container cover measures a pH of the content of the container.

10. The system of claim 1, wherein the container cover measures a temperature of the content of the container.

11. The system of claim 1, wherein the container is associated with a quantity measurement sensor included in one or more of the following: a clip, a sticker, a marker, a patch, and a zip lock mechanism.

12. The system of claim 1, wherein the process is further configured to receive receipt data from a scanner.

13. The system of claim 12, wherein analyzing to determine the analysis result includes analyzing the received receipt data.

14. The system of claim 12, wherein determining the analysis result includes analyzing the received receipt data and generating a shopping list based at least in part on the quantity identification and a determined consumption pattern.

15. The system of claim 1, wherein the action includes automatically reordering content of the container based on an automatically learned pattern of an amount of the content of the container needed and a time when the content of the container needs to be reordered determined using the analysis of the history of past quantity identifications received from the container cover over time.

16. The system of claim 1, wherein the action includes providing an indication of an expiration of the content of the container.

17. The system of claim 1, wherein the action includes providing a visual representation of a consumption pattern of the content of the container.

18. The system of claim 1, wherein the action includes providing a nutritional suggestion.

19. The system of claim 1, wherein the action includes providing a recipe recommendation.

20. The system of claim 1, wherein the action includes providing a reminder to purchase an additional quantity of the content of the container when it is determined that a user is near an applicable merchant.

21. The system of claim 1, wherein the determining of the quantity identification including by determining a magnitude value associated with an amount of distance traveled by the emitted signal comprises:

determining, using a lookup table, the quantity identification including by determining the magnitude value associated with an amount of distance traveled by the emitted signal, wherein the lookup table is determined based on a first consumable consumer product container or a second consumable consumer product container, and wherein the lookup table corresponding to the consumable consumer product container maps distances traveled to fill levels.

22. The system of claim 1, wherein the ignoring of the portion of the received version of the emitted signal comprises:

ignoring, for a predetermined amount of time, a beginning portion of the received version of the emitted signal to remove a signal resulting from coupling between the transmitter and the receiver.

23. The system of claim 1, wherein a distance from the one end of the waveguide to an opening of the waveguide is different from a distance from the one end of the receiving chamber to the opening of the receiving chamber.

24. The system of claim 1, wherein an opening of the waveguide is adjacent to the opening of the receiving chamber.

25. The system of claim 1, wherein a longitudinal axis of the waveguide is substantially parallel to a longitudinal axis of the receiving chamber.

26. A method for quantity analysis, comprising:

receiving a quantity identification of an amount of content included in a consumable consumer product container, wherein:

a container cover of the consumable consumer product container includes a transmitter configured to emit a signal into the consumable consumer product container using a waveguide;

the transmitter is located inside one end of the waveguide;

an acoustically transmissive liquid blocking material covers the transmitter;

the acoustically transmissive liquid blocking material blocks the content in the container from coming in contact with the transmitter and allows the signal emitted by the transmitter to at least in part pass through the acoustically transmissive liquid blocking material;

the container cover includes a receiver configured to be at least in part inside a neck of the consumable consumer product container when the container cover is engaged with the consumable consumer product container;

the receiver is located in a receiver chamber;

an opening of the receiver chamber is sealed by the acoustically transmissive liquid blocking material;

the acoustically transmissive liquid blocking material covering the transmitter is in the same vertical location as the opening of the receiver chamber;

the receiver is located inside one end of the receiver chamber;

the receiver chamber is separate from the waveguide;

the receiver is in a different vertical location as the transmitter;

the receiver is configured to receive a version of the signal emitted by the container cover;

the container cover is configured to determine the quantity identification including by determining a magnitude value associated with an amount of distance traveled by the emitted signal including by ignoring a portion of the received version of the emitted signal to at least in part ignore a coupling between the transmitter and the receiver and filtering at least a portion of the received version of the emitted signal to isolate a desired signal and detecting a signal peak in the isolated desired signal;

the container cover includes a battery and an accelerometer configured to detect a motion of the container cover; and the detected motion is utilized to optimize power consumed from the battery;

using a processor to analyze the quantity identification along with a history of past quantity identifications received from the container cover over time to determine an analysis result; and performing an action associated with the content of the container based on the analysis result.

27. A computer program product for quantity analysis, the computer program product being embodied in a non-transitory computer readable storage medium and comprising computer instructions for:

receiving a quantity identification of an amount of content included in a consumable consumer product container, wherein:

a container cover of the consumable consumer product container includes a transmitter configured to emit a signal into the consumable consumer product container using a waveguide;

the transmitter is located inside one end of the waveguide;

an acoustically transmissive liquid blocking material covers the transmitter;

the acoustically transmissive liquid blocking material blocks the content in the container from coming in contact with the transmitter and allows the signal emitted by the transmitter to at least in part pass through the acoustically transmissive liquid blocking material;

the container cover includes a receiver configured to be at least in part inside a neck of the consumable consumer product container when the container cover is engaged with the consumable consumer product container;

the receiver is located in a receiver chamber;

an opening of the receiver chamber is sealed by the acoustically transmissive liquid blocking material;

the acoustically transmissive liquid blocking material covering the transmitter is in the same vertical location as the opening of the receiver chamber;

the receiver is located inside one end of the receiver chamber;

the receiver chamber is separate from the waveguide;

the receiver is in a different vertical location as the transmitter;

the receiver is configured to receive a version of the signal emitted by the container cover;

the container cover is configured to determine the quantity identification including by determining a magnitude value associated with an amount of distance traveled by the emitted signal including by ignoring a portion of the received version of the emitted signal to at least in part ignore a coupling between the transmitter and the receiver and filtering at least a portion of the received version of the emitted signal to isolate a desired signal and detecting a signal peak in the isolated desired signal;

the container cover includes a battery and an accelerometer configured to detect a motion of the container cover; and the detected motion is utilized to optimize power consumed from the battery;

analyzing the quantity identification along with a history of past quantity identifications received from the container cover over time to determine an analysis result; and performing an action associated with the content of the container based on the analysis result.

* * * * *